US009650443B2

(12) United States Patent
Song et al.

(10) Patent No.: US 9,650,443 B2
(45) Date of Patent: May 16, 2017

(54) FUSION PROTEIN COMPRISING ANTI-C-MET ANTIBODY AND VEGF-BINDING FRAGMENT

(71) Applicant: Samsung Electronics Co., Ltd., Suwon-si, Gyeonggi-do (KR)

(72) Inventors: Yun Jeong Song, Seongnam-si (KR); Ho Yeong Song, Seongnam-si (KR); Seung Hyun Lee, Suwon-si (KR); Kyung Ah Kim, Seongnam-si (KR); Yun Ju Jeong, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 124 days.

(21) Appl. No.: 14/228,521

(22) Filed: Mar. 28, 2014

(65) Prior Publication Data

US 2014/0294837 A1 Oct. 2, 2014

(30) Foreign Application Priority Data

Mar. 28, 2013 (KR) ........................ 10-2013-0033872

(51) Int. Cl.

*C07K 16/46* (2006.01)
*A61K 39/00* (2006.01)
*C07K 16/28* (2006.01)
*C07K 14/71* (2006.01)

(52) U.S. Cl.

CPC .......... *C07K 16/2863* (2013.01); *C07K 14/71* (2013.01); *A61K 2039/505* (2013.01); *C07K 2317/10* (2013.01); *C07K 2317/24* (2013.01); *C07K 2317/515* (2013.01); *C07K 2317/52* (2013.01); *C07K 2317/53* (2013.01); *C07K 2317/56* (2013.01); *C07K 2317/565* (2013.01); *C07K 2317/622* (2013.01); *C07K 2317/75* (2013.01); *C07K 2317/76* (2013.01); *C07K 2317/92* (2013.01); *C07K 2319/00* (2013.01)

(58) Field of Classification Search

None

See application file for complete search history.

(56) References Cited

U.S. PATENT DOCUMENTS 6,676,941 B2 1/2004 Thorpe et al.
7,070,959 B1 7/2006 Papadopoulos et al.
7,087,411 B2 8/2006 Daly et al.
7,279,159 B2 10/2007 Daly et al.
7,306,799 B2 12/2007 Wiegand et al.
7,374,757 B2 5/2008 Papadopoulos et al.
7,374,758 B2 5/2008 Papadopoulos et al.
7,396,664 B2 7/2008 Daly et al.
7,399,612 B2 7/2008 Daly et al.
7,514,537 B2 4/2009 Jensen
7,521,049 B2 4/2009 Wiegand et al.
7,524,499 B2 4/2009 Papadopoulos et al.
7,615,215 B2 11/2009 Shitara et al.
7,635,474 B2 12/2009 Daly et al.
7,732,570 B2 6/2010 Hinton et al.
7,771,721 B2 8/2010 Davis-Smyth et al.
7,786,270 B2 8/2010 Johnson et al.
7,790,399 B2 9/2010 Bourel et al.
7,858,739 B2 12/2010 Chen et al.
7,960,512 B2 6/2011 Stavenhagen et al.
7,964,377 B2 6/2011 Papadopoulos et al.
7,972,598 B2 7/2011 Daly et al.
7,998,931 B2 8/2011 Van Bruggen et al.
8,003,774 B2 8/2011 Stavenhagen et al.
8,007,799 B2 8/2011 Van Bruggen et al.
8,029,791 B2 10/2011 Papadopoulos et al.
8,034,905 B2 10/2011 Kavlie et al.
8,039,595 B2 10/2011 Kanda et al.
8,084,234 B2 12/2011 Papadopoulos et al.
8,119,604 B2 2/2012 Gombotz et al.
8,119,770 B2 2/2012 Blanche et al.
8,563,696 B2 10/2013 Cheong et al.
2001/0039479 A1 11/2001 Jardetzky et al.
2003/0003502 A1 1/2003 Jardetzky et al.
2003/0171546 A1 9/2003 Jensen
2003/0207391 A1 11/2003 Pappa
2004/0241160 A1 12/2004 Wu et al.
2004/0242851 A1 12/2004 Zhu
2005/0053599 A1 3/2005 Van Bruggen et al.
2005/0123537 A1 6/2005 Thorpe et al.
2005/0244405 A1 11/2005 Van Bruggen et al.
2007/0258980 A1 11/2007 Van Bruggen et al.
2008/0187529 A1 8/2008 Shitara et al.
2008/0299116 A1 12/2008 Van Bruggen et al.
(Continued)

FOREIGN PATENT DOCUMENTS

EP 2316484 A1 5/2011
KR 2011-0047698 A 5/2011
WO WO 2009/134776 A2 11/2009
WO WO 2012/069557 A1 5/2012
WO 2012/162561 A2 11/2012

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
(Continued)

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

There are provided a fusion protein formed by coupling of anti-c-Met antibody and VEGF-binding fragment, a bispecific antibody comprising the fusion protein, a polynucleotide encoding the fusion protein, a transformant comprising the polynucleotide, a pharmaceutical composition comprising the bispecific antibody as an active ingredient, and a method for preparing the bispecific antibody which is targeted at c-Met and VEGF at the same time, with improved anticancer and anti-angiogenesis effects, comprising coupling an anti-c-Met antibody with a VEGF-binding fragment.

17 Claims, 11 Drawing Sheets

(56) References Cited

U.S. PATENT DOCUMENTS

2009/0028859 A1 1/2009 Zhu
2009/0257994 A1 10/2009 Jensen
2009/0264358 A1 10/2009 Yu
2010/0076178 A1 3/2010 Ghayur et al.
2010/0260668 A1 10/2010 Ghayur et al.
2010/0303793 A1 12/2010 Olszewska-Pazdrak et al.
2010/0331250 A1 12/2010 Zhou et al.
2010/0331527 A1 12/2010 Davis et al.
2011/0104161 A1 5/2011 Burgess et al.
2011/0104176 A1 5/2011 Cheong et al.
2011/0177070 A1 7/2011 Lofquist et al.
2011/0195454 A1 8/2011 McWhirter et al.
2011/0223129 A1 9/2011 Jensen
2011/0257035 A1 10/2011 Pena
2011/0263442 A1 10/2011 Akervall
2011/0268735 A1 11/2011 Scaria et al.
2011/0281748 A1 11/2011 Singh et al.
2012/0014957 A1 1/2012 Ghayur et al.
2012/0021409 A1 1/2012 McWhirter et al.
2013/0236467 A1 9/2013 Griggs et al.

OTHER PUBLICATIONS

Wu et al. (1999). J. Mol. Biol. 294:151-162.*

Rudikoff et al. (1982). PNAS. 79:1979-1983.*

European Patent Office, Extended European Search Report in European Patent Application No. 14154457.7, Nov. 11, 2014, 14 pp.

Carter et al., "Improving the Efficacy of Antibody-Based Cancer Therapies", *Nature Reviews*, 1(2), 118-129 (2001).

Alitalo, K., "The Lymphatic Vasculature in Disease", *Nature Medicine*, 17(11), 1371-1380 (2011).

Database Geneseq (online) "Human Fms-related tyrosine kinase 1 (VEGFR-1) protein, Seq:1.", XP002731861, retrieved from EBI accession No. GSP:AYJ81126 (Nov. 25, 2010).

European Patent Office, Office Action in European Patent Application No. 14154457.7, Mar. 11, 2016, 4 pp.

European Patent Office, Partial European Search Report in European Patent Application No. 14154457.7, Aug. 4, 2014, 6 pp.

* cited by examiner

FUSION PROTEIN COMPRISING ANTI-C-MET ANTIBODY AND VEGF-BINDING FRAGMENT

CROSS-REFERENCE TO RELATED APPLICATIONS

This application claims the benefits of Korean Patent Application No. 10-2013-0033872, filed on Mar. 28, 2013, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 161,462 Byte ASCII (Text) file named "715587_ST25 revised_20151104.TXT" created on Nov. 4, 2015.

BACKGROUND OF THE INVENTION

1. Field

Provided are a fusion protein comprising an anti-c-Met antibody and a VEGF-binding fragment which are coupled to each other, a bispecific antibody comprising the fusion protein, a polynucleotide encoding the fusion protein, a transformant comprising the polynucleotide, a pharmaceutical composition comprising the bispecific antibody as an active ingredient, and a method for preparing the bispecific antibody targeting c-Met and VEGF at the same time and has improved anticancer and anti-angiogenesis effects, comprising coupling an anti-c-Met antibody with a VEGF-binding fragment.

2. Description of the Related Art c-Met is a receptor tyrosine kinase (RTK) present at the surface of cells, and binds to its ligand, hepatocyte growth factor (HGF), to promote intracellular signal transduction, thereby promoting the growth of cells. In addition, c-Met is over-expressed in cancer cells, and thereby widely implicated in cancer incidence, cancer metastasis, cancer cell migration, cancer cell invasion, angiogenesis, etc. c-Met is over-expressed in many kinds of cancers and, in particular, most of the patients with over-expressed c-Met tend to have poor prognosis.

Vascular endothelial cell growth factor (VEGF) is also present in normal cells and, in particular, it is secreted from cancer cells and binds to its receptor, VEGF Receptor (VEGFR) to induce angiogenesis, whereby cancer cells are supplied with nutrients necessary for their growth through newly induced blood vessels.

Therefore, both of c-Met and VEGF are of great importance as targets in developing anticancer drugs. There remains a need for development of bispecific antibodies targeting c-Met and VEGF at the same time and therapeutic technologies using the same.

BRIEF SUMMARY OF THE INVENTION

One embodiment provides a fusion protein comprising (a) an anti-c-Met antibody or an antigen-binding fragment of the anti-c-Met antibody and (b) a VEGF-binding fragment.

Another embodiment provides a bispecific antibody targeting c-Met and VEGF, comprising the fusion protein.

Another embodiment provides a polynucleotide encoding the fusion protein.

Another embodiment provides a transformant comprising the polynucleotide.

Another embodiment provides a pharmaceutical composition comprising the bispecific antibody as an active ingredient.

Still another embodiment provides a method of preparing a bispecific antibody targeting c-Met and VEGF and having improved anticancer and anti-angiogenesis effects, comprising coupling an anti-c-Met antibody with a VEGF-binding fragment.

Also provided is a method of preventing or treating a disease induced by c-Met or VEGF comprising administering a pharmaceutical amount of the bispecific antibody to a patient in need thereof.

DETAILED DESCRIPTION OF THE INVENTION

Figure 1:
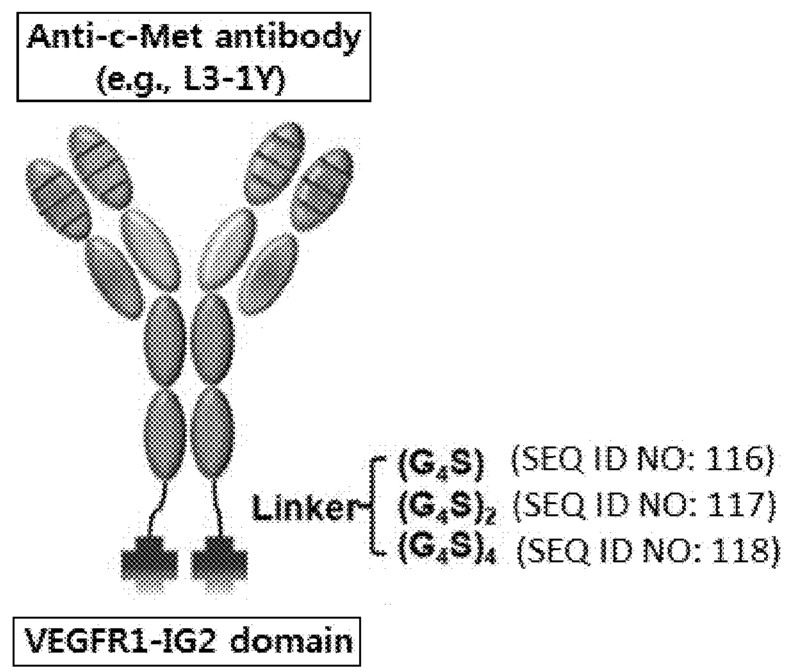
FIG. 1 is a schematic view showing one embodiment of a bispecific antibody.

The present invention can effectively inhibit the growth of cancer cells and angiogenesis by providing a bispecific antibody capable of binding to c-Met and VEGF at the same time, where the bispecific antibody targets c-Met and VEGF at the same time, thereby leading to improved anticancer effects and/or angiogenesis inhibitory effects.

The bispecific antibody capable of binding to c-Met and VEGF at the same time can inhibit the growth itself of cancer cells by targeting c-Met, and at the same time, it can block angiogenesis and prevent the supply of nutrients essential for the growth of cancer cells by targeting VEGF, to inhibit the growth of the cancer cells again, thereby leading to more enhanced synergistic effects in inhibition of cancer cell growth and/or inhibition of angiogenesis.

One embodiment provides a fusion protein comprising an anti-c-Met antibody and a VEGF-binding fragment. The anti-c-Met antibody may include an antigen-binding fragment of an anti-c-Met antibody and a modified form of the antibody, as well as an anti-c-Met antibody. Therefore, the fusion protein may be one formed by coupling of a VEGF-binding fragment, and an anti-c-Met antibody, an antigen-binding fragment of the antibody, or a modified form of the antibody.

In another embodiment, a method of using the fusion protein as a bispecific (dual-targeting) antibody capable of binding to c-Met and VEGF at the same time is provided. In particular, there is provided a bispecific antibody against c-Met and VEGF, comprising a fusion protein formed by coupling of VEGF-binding fragment, and anti-c-Met antibody, an antigen-binding fragment of the antibody, or a modified form of the antibody.

In still another embodiment, there are provided a polynucleotide encoding the fusion protein and a transformant transduced with the polynucleotide. The transformant can be used for the production of the fusion protein or the bispecific antibody.

In still another embodiment, there is provided a pharmaceutical composition comprising the fusion protein or the bispecific antibody as an active ingredient. The pharmaceutical composition may have prevention and/or treatment effects against c-Met and/or VEGF induced diseases. For example, the pharmaceutical composition may be an anticancer drug or an angiogenesis inhibitor.

In still another embodiment, there is provided a method for preventing and/or treating c-Met and/or VEGF induced diseases, comprising administering a therapeutically effective amount of the fusion protein or the bispecific antibody.

In still another embodiment, there is provided a method for preparing a bispecific antibody targeting c-Met and VEGF at the same time and having improved anticancer and anti-angiogenesis effects, comprising culturing the transformant to express the fusion protein, or coupling an anti-c-Met antibody, an antigen-binding fragment of the antibody, or a modified form of the antibody with a VEGF-binding fragment.

In still another embodiment, there is provided a method for preparing c-Met antibody with improved anticancer effects and/or angiogenesis inhibitory effects, by coupling an anti-c-Met antibody, an antigen-binding fragment of the antibody, or a modified form of the antibody with a VEGF-binding fragment.

In still another embodiment, there is provided a composition for detection of c-Met and/or VEGF, comprising the fusion protein as an active ingredient.

In still another embodiment, there is provided a composition for diagnosis of c-Met and/or VEGF induced diseases, comprising the fusion protein as an active ingredient.

VEGF is present in normal cells and particularly, it is secreted from cancer cells and binds to its receptor (VEGFR: VEGF Receptor) to induce angiogenesis, and cancer cells are supplied with nutrients necessary for their growth through newly induced blood vessels. The over-expression of VEGF becomes a cause of various diseases and it is involved with not only cancer incidence but also its bad prognosis such as invasion, metastasis, and so on. For such reasons, VEGF has become a key target in anticancer therapy.

VEGF may originate from mammals including primates such as humans and monkeys, and rodents such as mice and rats. For example, the VEGF proteins may be a polypeptide encoded by a nucleotide sequence (mRNA) provided by GenBank Accession Number NM_001025366.2, NM_001025367.2, NM_001025368.2, NM_001025369.2, NM_001025370.2, NM_001033756.2, NM_001171622.1, NM_001171623.1, NM_001171624.1, NM_001171625.1, NM_001171626.1, NM_001171627.1, NM_001171628.1, NM_001171629.1, NM_001171630.1, NM_001204384.1, NM_001204385.1, NM_003376.5, etc.

The "c-Met" or "c-Met protein" refers to a receptor tyrosine kinase (RTK), which binds hepatocyte growth factor (HGF). The c-Met protein may originate from any kinds of species, and for example, it may originate from primates, such as human c-Met (e.g., NP_000236) or monkey c-Met (e.g., *Macaca mulatta*, NP_001162100), or rodents such as mouse c-Met (e.g., NP_032617.2) or rat c-Met (e.g., NP_113705.1). For example, c-Met proteins may include a polypeptide encoded by the nucleotide sequence identified as GenBank Accession Number NM_000245, or a polypeptide including the amino acid sequence identified as GenBank Accession Number NP_000236, or extracellular domains thereof. The receptor tyrosine kinase c-Met is implicated in several mechanisms, for example, cancer incidence, cancer metastasis, cancer cell migration, cancer cell invasion, angiogenesis, etc.

The anti-c-Met antibody is a protein specifically recognizing c-Met, and may be a single-targeting antibody recognizing c-Met only. A detailed explanation thereof is as follows.

The antigen-binding fragment of the anti-c-Met antibody may be selected from the group consisting of complementarity determining region (CDR), a combination of CDR and Fc region, scFv, $(scFv)_2$, Fab, Fab', or $F(ab')_2$ of the anti-c-Met antibody, which is described below.

When the anti-c-Met antibody is used, the VEGF-binding fragment may be coupled to the C-terminus of the anti-c-Met antibody either through a suitable peptide linker or without it. Also, when an antigen-binding fragment of the anti-c-Met antibody is used, the VEGF-binding fragment may be coupled to either the N-terminus or the C-terminus of the antigen-binding fragment of the anti-c-Met antibody, and it may be coupled through a suitable peptide linker or without it.

A modified form of the antibody may include isotypes of human and animal antibodies present in nature and/or Fc of any human antibodies (e.g., IgG1, IgG2, and the like) or animal antibodies in which one or more amino acids constituting a hinge portion are modified. Unless mentioned differently herein, the anti-c-Met antibody may be understood to include such modified forms.

The VEGF-binding fragment of the fusion protein may be a molecule that binds to VEGF, for example, a VEGF-binding protein such as a VEGF receptor, anti-VEGF antibody, and the like, or a fragment including a VEGF-binding region of the VEGF-binding protein, for example, an antigen-binding fragment of the anti-VEGF antibody or a VEGF-binding region of the VEGF receptor. For example, the anti-VEGF antibody may be Bevacizumab, and the antigen-binding fragment of the anti-VEGF antibody may be selected from the group consisting of a complementarity determining region (CDR) or variable region thereof, a combination of a CDR or variable region and Fc region thereof, or an scFv, $(scFv)_2$, Fab, Fab', or $F(ab')_2$ fragment of the anti-VEGF antibody. The VEGF receptor may be, for example, human VEGF receptor 1 (P17948.2; SEQ ID NO: 109), human VEGF receptor 2 (P35968.2), human VEGF Receptor 3 (P35916.3), and the like. Also, the fragment including a VEGF-binding region of the VEGF-binding protein may be second Ig-like domain 2 (VIG2) or a polypeptide including the VIG2 region within the VEGF receptor. For example, the fragment including the VEGF-binding region of human VEGF receptor 1 may be second Ig-like domain 2 (VIG2; e.g., an amino acid sequence (SEQ ID NO: 110) from $129^{th}$ to $229^{th}$ positions of the amino acid sequence (SEQ ID NO: 109; P17948.2)), or a polypeptide including 102 to 1338 consecutive amino acids containing the VIG2 (SEQ ID NO: 110) within the amino acid sequence of SEQ ID NO: 109.

Accordingly, in a concrete embodiment, the VEGF-binding fragment may be an anti-VEGF antibody such as Bevacizumab and the like, an antigen-binding fragment of the anti-VEGF antibody selected from the group consisting of complementarity determining region (CDR), a combination of CDR and Fc region, scFv, $(scFv)_2$, Fab, Fab', or $F(ab')_2$ of the anti-VEGF antibody, a VEGF receptor (e.g., SEQ ID NO: 109), or a VEGF-binding region of the VEGF receptor (e.g., VIG2 of SEQ ID NO: 110, or polypeptide including 102 to 1338 consecutive amino acids including VIG2 of SEQ ID NO: 110 within the amino acid sequence of SEQ ID NO: 109).

In a concrete embodiment, the fusion protein or the bispecific antibody may be formed by coupling a Fc region of an anti-c-Met antibody as described below, an antigen-binding fragment, or a modified form (variant) thereof with a VEGF-binding fragment, e.g., VIG2 (see FIG. 1).

The anti-c-Met antibody, an antigen-binding fragment of the antibody, or a modified form of the antibody, and the VEGF-binding fragment may be coupled through a linker. The linker may be a peptide linker in length of 1 to about 100 amino acids, particularly about 2 to about 50 amino acids, more particularly about 5 to about 30 amino acids. For example, the peptide linker may include one or more amino acids selected from the group consisting of Gly, Asn, Ser, Thr, and Ala, but not be limited thereto. In a specific embodiment, the linker may be expressed as (GGGGS)n (SEQ ID NO: 116), wherein n is the repeat number of (GGGGS) (SEQ ID NO: 116) units, and in consideration of the efficacy of the bispecific antibody, n may be 1 to about 10, particularly 1 to about 5.

The present invention is characterized by enhancing the pharmacological effects of c-Met antibody by coupling the c-Met antibody or a fragment thereof with a VEGF-binding fragment (e.g., VIG2) to manufacture a bispecific antibody.

The anti-c-Met antibody used in the fusion protein or the bispecific antibody may be any anti-c-Met antibody or any antigen-binding fragment thereof. In particular, the anti-c-Met antibody may recognize a specific region of c-Met, for example a specific region within the SEMA domain, as an epitope. The anti-c-Met antibody may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may include the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope," as used herein, refers to an antigenic determinant, which is a part of an antigen recognized by an antibody. In one embodiment, the epitope may be a region comprising 5 or more contiguous (consecutive or non-consecutive) amino acid residues within the SEMA domain (SEQ ID NO: 79) of c-Met protein, for instance, 5 to 19 consecutive amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti-c-Met antibody may specifically bind to an epitope which has 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody may be an antibody or an antigen-binding fragment thereof, which includes:

(a) a heavy chain variable region comprising at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids comprising amino acid residues from the 3$^{rd}$ to 10$^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids comprising amino acid residues from the 1$^{st}$ to 6$^{th}$ positions of SEQ ID NO: 85; and (b) a light chain variable region comprising at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 86, or an amino acid sequence including 9-17 consecutive amino acids comprising amino acid residues from the 1$^{st}$ to 9$^{th}$ positions of SEQ ID NO: 89.

Herein, the amino acid sequences of SEQ ID NOS: 4 to 9 are respectively represented by following Formulas I to VI, below:

$Xaa_1$-$Xaa_2$-Tyr-Tyr-Met-Ser(SEQ ID NO: 4), Formula I wherein $Xaa_1$ is absent or Pro or Ser, and $Xaa_2$ is Glu or Asp, Arg-Asn-$Xaa_3$-$Xaa_4$-Asn-Gly-$Xaa_5$-Thr(SEQ ID NO: 5), Formula II wherein $Xaa_3$ is Asn or Lys, $Xaa_4$ is Ala or Val, and $Xaa_5$ is Asn or Thr, Asp-Asn-Trp-Leu-$Xaa_6$-Tyr(SEQ ID NO: 6), Formula III wherein $Xaa_6$ is Ser or Thr, Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7), Formula IV wherein $Xaa_7$ is His, Arg, Gln, or Lys, $Xaa_8$ is Ser or Tip, $Xaa_9$ is His or Gln, and $Xaa_{10}$ is Lys or Asn, Trp-$Xaa_{11}$-Ser-$Xaa_{12}$-Arg-Val-$Xaa_{13}$(SEQ ID NO: 8), Formula V wherein $Xaa_{11}$ is Ala or Gly, $Xaa_{12}$ is Thr or Lys, and $Xaa_{13}$ is Ser or Pro, and $Xaa_{14}$-Gln-Ser-Tyr-Ser-$Xaa_{15}$-Pro-$Xaa_{16}$-Thr(SEQ ID NO: 9), Formula VI wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or the antigen-binding fragment may include a heavy variable region including a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light variable region including a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies include been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still include variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti-c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be synthetic or recombinant.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ϵ) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin.

The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In one embodiment, the antibody may be an antigen-binding fragment selected from the group consisting of CDR, a combination of CDR and Fc region, scFv, $(scFv)_2$, Fab, Fab', and $F(ab')_2$.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The $F(ab')_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv.

The antigen-binding fragments may be attainable using protease (for example, the Fab fragment may be obtained by restricted cleavage of a whole antibody with papain, and the $F(ab')_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, ten, or more) amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104 (U8-HC5), or a hinge region including the amino acid sequence of SEQ ID NO: 105 (non-modified human hinge). Preferably, the hinge region has the amino acid sequence of SEQ ID NO: 100 or 101.

The heavy chain constant region and the light chain constant region other than the CDR region, the heavy chain variable region, or the light chain variable region may be the heavy chain constant region and the light chain constant region of any subtype of immunoglobulin (e.g., IgA, IgD, IgE, IgG (IgG1, IgG2, IgG3, IgG4), IgM, etc.).

In one embodiment of the anti-c-Met antibody or antigen-binding fragment, the variable domain of the heavy chain has the amino acid sequence of SEQ ID NO: 17, 74, 87, 90, 91, 92, 93, or 94 and the variable domain of the light chain has the amino acid sequence of SEQ ID NO: 18, 19, 20, 21, 75, 88, 95, 96, 97, 98, 99, or 107.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the entire disclosures of which are incorporated herein by reference). The anti-c-Met antibody may include all the antibodies defined in Korean Patent Publication No. 2011-0047698.

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 62 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

In another embodiment, the anti-c-Met antibody may include a light chain variable region including the amino acid sequence of SEQ ID NO: 106, a variable domain of a light chain including the amino acid sequence of SEQ ID NO: 107, or a light chain including the amino acid sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) of SEQ ID NO: 108 with tryptophan. By such replacement, antibodies and antibody fragments comprising such sequences exhibit increased activities, such as c-Met biding affinity, c-Met degradation activity, Akt phosphorylation inhibition, and the like.

In a specific embodiment, the fusion protein or the bispecific antibody may be those formed by coupling the Fc portion of the anti-c-Met antibody or the N-terminal or C-terminal of an antigen-binding fragment of the antibody with a VEGF-binding fragment (e.g., VIG2) via a peptide linker or without it (see FIG. 1).

In a specific embodiment, the fusion protein or the bispecific antibody may include (a) a heavy chain including the amino acid sequence of SEQ ID NO: 62, the amino acid sequence from the $18^{th}$ to $462^{nd}$ positions of SEQ ID NO: 62, the amino acid sequence of SEQ ID NO: 64, the amino acid sequence from $18^{th}$ to $61^{st}$ positions of SEQ ID NO: 64, the amino acid sequence of SEQ ID NO: 66, or the amino acid sequence from $18^{th}$ to $460^{th}$ positions of SEQ ID NO: 66, and (b) a light chain including the amino acid sequence of SEQ ID NO: 68, the amino acid sequence from $21^{st}$ to $240^{th}$ positions of SEQ ID NO: 68, the amino acid sequence of SEQ ID NO: 70, the amino acid sequence from $21^{st}$ to $240^{th}$ positions of SEQ ID NO: 70, or the amino acid sequence of SEQ ID NO: 108.

The VEGF-binding fragment (e.g., VIG2 or a polypeptide including VIG2) is confirmed not only to enhance antibody efficacy but also to remarkably reduce side effects (agonism), even when it is coupled to other anti-c-Met antibodies besides the anti-c-Met antibody as mentioned above (see FIG. 5).

In particular, the c-Met antibodies of which the antibody efficacy and agonism can be improved by being coupled with VEGF-binding fragment may be any one selected from all anti-c-Met antibodies other than the above-described anti-c-Met antibody as well as the above-described anti-c-Met antibody. For example the other anti-c-Met antibody may be one including (a) a heavy chain including the amino acid sequence of SEQ ID NO: 112 or SEQ ID NO: 114 and (b) a light chain including the amino acid sequence of SEQ ID NO: 113 or SEQ ID NO: 115, more particularly, including (a) a heavy chain including a heavy chain including the amino acid sequence of SEQ ID NO: 112 and (b) a light chain including the amino acid sequence of SEQ ID NO: 113, or including (a) a heavy chain including the amino acid sequence of SEQ ID NO: 114 and (b) a light chain including the amino acid sequence of SEQ ID NO: 115.

The fusion protein formed by coupling of the VEGF-binding fragment, and the anti-c-Met antibody or an antigen-binding fragment of the antibody through a linker or without a linker can be used as a precursor for preparing a bispecific antibody which targets c-Met and VEGF at the same time. The pharmaceutical composition may include a pharmaceutically effective amount of the bispecific antibody, together with a pharmaceutically acceptable carrier, diluent, and/or excipient.

The pharmaceutically acceptable carrier included in the pharmaceutical composition may be any commonly used in the formulations of drugs, and may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, mineral oil, and the like, but not limited thereto. Besides these ingredients, the pharmaceutical composition may further include one or more selected from the group consisting of a diluent, an excipient, a lubricant, a wetting agent, a sweetener, a flavor enhancer, an emulsifying agent, a suspension agent, and a preservative.

The pharmaceutical composition may be administered through oral or parenteral route. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the composition for oral administration must be coated or formulated to prevent digestion in stomach. In addition, the composition may be administered using an optional device capable of delivering an active substance to target cells.

The term "the pharmaceutically effective amount" as used herein refers to an amount at which each active ingredient can exert pharmaceutically significant effects.

The pharmaceutical composition may be administered to mammals including primates such as humans and monkeys and rodents such as rats and mice.

The effective amount of the bispecific antibody in the pharmaceutical composition for a single dose may be prescribed in a variety of ways, depending on factors such as formulation methods, administration manners, age of patients, body weight, gender, pathologic conditions, diets, administration time, administration interval, administration route, excretion speed, and reaction sensitivity. For example, the effective amount of the bispecific antibody for a single dose may be in the range of 0.1 to 50 mg/kg, particularly 1 to 20 mg/kg. The effective amount for the single dose may be formulated into a single formulation in a unit dosage form or formulated in suitably divided dosage forms. Alternatively, the pharmaceutical composition may be manufactured to be contained in a multiple dosage container.

The pharmaceutical composition may be a solution in an oil or an aqueous medium, a suspension, a syrup, an emulsifying solution form, or it may be formulated into the form of an extract, powders, granules, a tablet or a capsule, and it may further include a dispersing agent or a stabilizing agent for formulation.

In particular, the pharmaceutical composition may be formulated into an immunoliposome since it contains a bispecific antibody. A liposome containing an antibody may be prepared using any methods well known in the pertinent field. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction. A chemical drug, such as doxorubicin, may be further included in the liposome.

The pharmaceutical composition described herein can be used for preventing and/or treating diseases induced by c-Met and VEGF, for example, diseases induced by an increase in copy number and/or increased expression (e.g., overexpression) of c-Met and/or over-expression of VEGF, and particularly, a cancer or metastasis of a cancer. The cancer may be those showing over-expression of c-Met and/or VEGF, and they may include, without limitation, one or more selected from the group consisting of solid cancers, such as, squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, stomach cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, osteosarcoma, and the like. In a particular embodiment, the cancer may be brain cancer, stomach cancer, kidney cancer, or lung cancer (e.g., small-cell lung cancer, non-small-cell lung cancer, adenocarcinoma of the lung, squamous cell carcinoma of the lung, etc.). The cancer may include a metastatic cancer, as well as a primary cancer. In another embodiment, the diseases induced by c-Met and VEGF may be gestational diabetes, diabetic retinopathy, macular degeneration (e.g., wet age-related macular degeneration: wet AMD) and so on.

Thus, a method of preventing and/or treating a c-Met and/or VEGF induced disease is provided, wherein the method comprises administering a pharmaceutically effective amount of the fusion protein or the bispecific antibody to a patient in need of the prevention and/or treatment of c-Met and/or VEGF induced diseases. The prevention and/or treatment method may further include the step of identifying a patient in need of the prevention and/or treatment of c-Met and/or VEGF induced diseases, prior to the administration step.

In addition, the anti-c-Met antibody can function independently from Cbl which is a typical RTK negative regulator, and exhibit c-Met degradation activity via a lysosome pathway, not via a proteasome pathway which is mediated by Cbl. Thus, even if it is administered to patients where Cbl does not normally function due to a mutation of Cbl, an insufficient expression amount of Cbl, a mutation of Cbl binding region of c-Met, and the like, c-Met can be suppressed through the LRIG1 mediator which is another negative regulator functioning independently from Cbl. Accordingly, the administration of the bispecific antibody comprising the anti-c-Met antibody may be particularly advantageous to the patients where Cbl does not function normally.

Also provided herein is a polynucleotide encoding a fusion protein comprising an anti-c-Met antibody or antigen-binding fragment thereof and a VEGF-binding fragment, as well as a recombinant vector comprising the polynucleotide and a recombinant cell containing the polynucleotide or vector. All aspects of the c-Met antibody and antibody fragment, and the VEGF-binding fragment, are as described herein with respect to the fusion protein. The nucleic acid, vector, and host cell can be used for any purpose, for instance, a method of preparing the fusion protein by expressing the nucleic acid or vector in the host cell.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), a phage (for example, λgt4λB, λ-Charon, λΔz1, M13, and the like), or a virus (for example, SV40, and the like), but not be limited thereto.

In the recombinant vector, the polynucleotides may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed for either cloning or expression in a conventional manner. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, $pL^{\lambda}$ promoter, CMV promoter, trp promoter, lac promoter, tac promoter, T7 promoter, and the like), a ribosome binding site for initiating translation, and a transcription/translation termination sequence. When a eukaryotic cell is used as a host cell, the vector used generally includes the origin of replication acting in the eukaryotic cell, for example, a fl replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter, and the like) or a promoter derived from mammalian viruses (for example, an adenovirus late promoter, a vaccinia virus 7.5K promoter, a SV40 promoter, a cytomegalovirus promoter, a tk promoter of HSV, and the like). A transcription termination sequence in an expression vector for a eukaryotic host cell may be, in general, a polyadenylation sequence.

The recombinant cell may be obtained by transfecting the recombinant vector into a suitable host cell. Any host cells known in the pertinent art to enable stable and continuous cloning or expression of the recombinant vector may be used as the host cell. Suitable prokaryotic host cells may be one or more selected from *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis*, or *Bacillus thuringiensis*, intestinal bacteria and strains such as *Salmonella typhymurum, Serratia marcescens*, and various *Pseudomonas* species. Suitable eukaryotic host cells to be transformed may be one or more selected from yeasts, such as *Saccharomyces cerevisiae*, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines, but not be limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

In another aspect, provided is a method of preparing an anti-c-Met antibody with improved c-Met inhibition, anticancer effects, and/or angiogenesis inhibitory effects, or a method of improving c-Met inhibition and/or angiogenesis inhibitory effects of an anti-c-Met antibody, including coupling an anti-c-Met antibody or an antigen-binding fragment thereof (or a modified form of the antibody) with a VEGF-binding fragment as described herein. The coupling can be effected by any suitable technique, such as by synthesizing a nucleic acid encoding the c-Met antibody or fragment thereof and the VEGF-binding fragment as a fusion protein, optionally including a linker sequence between the c-Met antibody and the VEGF-binding fragment.

When an existing anti-c-Met antibody is coupled with a portion capable of binding to VEGF (for example, Ig-like domain 2: VIG2 (e.g., SEQ ID NO: 110) of human VEGF Receptor 1 (e.g., SEQ ID NO: 109) or a polypeptide comprising 102 to 1338 consecutive amino acids containing SEQ ID NO: 110 among SEQ ID NO: 109), to be manufactured as a bispecific (dual-targeting) antibody form that targets c-Met and VEGF at the same time, it is confirmed that the bispecific antibody exhibits synergistic effects while maintaining the effect of targeting each of c-Met and VEGF.

Accordingly, the manufacturing technology of the bispecific antibody proposed in this invention may improve the anticancer effects of anti-c-Met antibodies.

The thus prepared bispecific antibody can more efficiently inhibit the growth of cancer cells than the anti-c-Met antibody alone, and even when bispecific antibodies as described above were manufactured using various kinds of anti-c-Met antibodies, it was confirmed that they exhibited superior effects to the single antibodies (see Example 5). That is, the manufacturing method of the bispecific antibody proposed in this invention is generally applicable to enhance the anticancer effects of the anti-c-Met antibodies.

The bispecific antibodies maintained c-Met binding related properties including anticancer and anti-angiogenesis effects of the existing anti-c-Met antibodies (see Example 2). Also, the bispecific antibodies antagonized the biological functions of VEGF by including a VEGF-binding region (see Example 3). Furthermore, the anticancer effects of the bispecific antibodies were confirmed to be superior to the anti-c-Met antibodies through animal model-based tests (see Example 4).

Figure 4A:
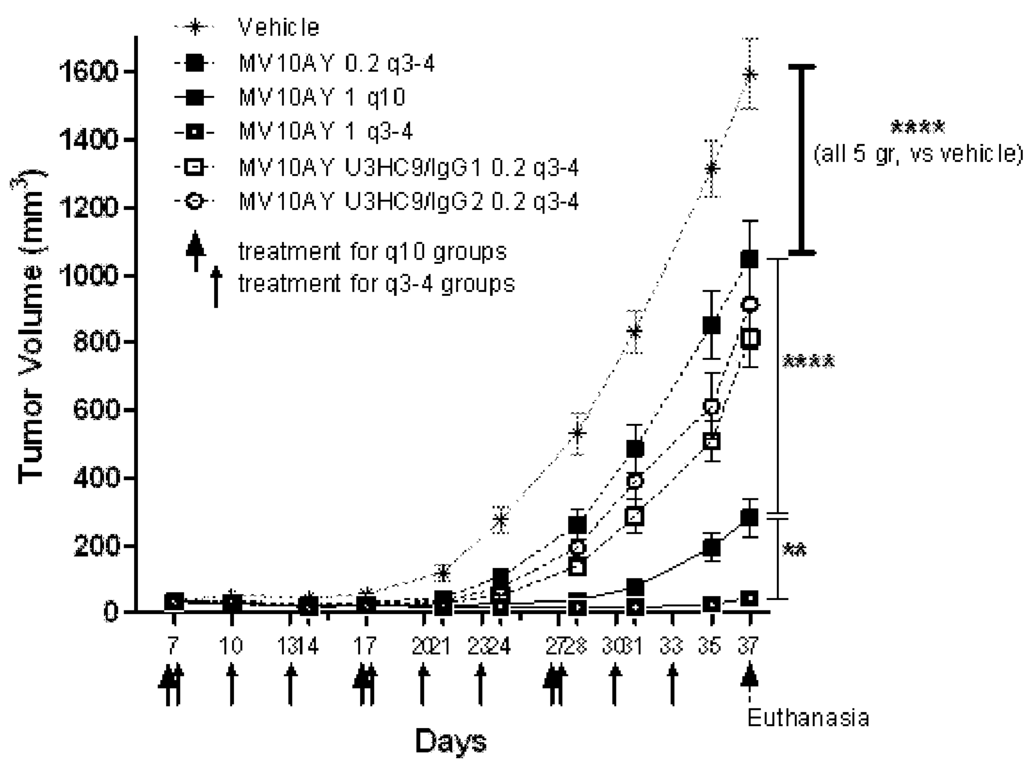
FIG. 4A illustrates the in vivo anticancer effects of the bispecific antibody prepared in one example against U87-MG brain cancer cells. The upper portion of FIG. 4A illustrates tumor volumes according to time. The lower portion of FIG. 4A illustrates the weights of the tumors that were extracted after completion of the experiment
Figure 4A:
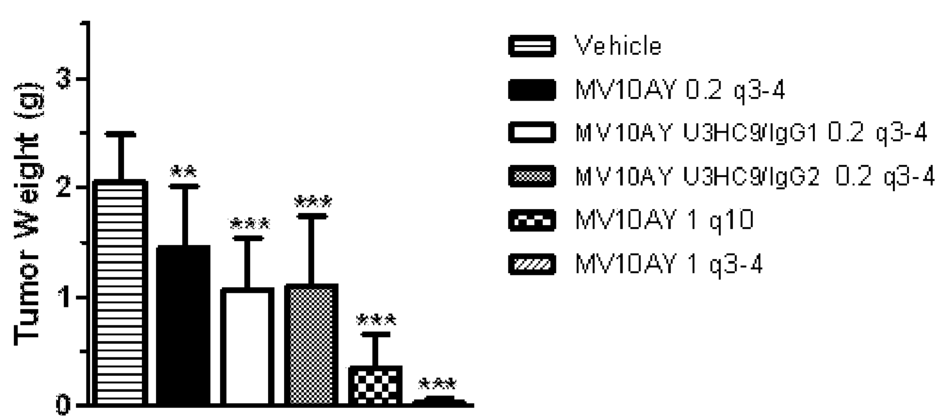

Further, even in the cases of various forms of anti-c-Met antibodies (different linkers, different lengths, modified Fc portion, different CDR, etc.), they exhibited similar effects when coupled with VIG2 (see FIG. 4A).

In this respect, the method of attaching the VEGF-binding region to the anti-c-Met antibody is expected to be generally applicable to enhance the anticancer and anti-angiogenesis effects of anti-c-Met antibodies.

Also, as the fusion protein and/or the bispecific antibody enable simultaneous detection of c-Met and VEGF, they are useful in the simultaneous detection of c-Met and VEGF, and diagnosis of c-Met and VEGF induced diseases. An embodiment provides a method of detecting c-Met and VEGF or diagnosing a c-Met and VEGF induced disease, including contacting the fusion protein and/or the bispecific antibody to a sample, and measure the level of binding of the fusion protein and/or the bispecific antibody and both of c-Met and VEGF.

As the technology of coupling the anti-c-Met antibody with the VEGF-binding region provided in this invention enhances anticancer/angiogenesis inhibitory effects of the anti-c-Met antibody, it can be used for the development of anticancer drugs applicable to brain cancers, lung cancers, stomach cancers, etc., and drugs of diseases induced by angiogenesis mechanism. Additionally, this technology can be used for the development of drugs against diseases with which c-Met/HGF signal transduction system and VEGF/VEGFR signal transduction system are associated. Accordingly, excellent effects can be achieved, as well as simple administration using the bispecific antibody when compared to the co-administration of related drugs.

One or more embodiments of the present invention will now be described in further detail with reference to the following Examples. However, these examples are for the illustrative purposes only and are not intended to limit the scope of the invention.

EXAMPLES

Reference Example 1

Construction of Anti-c-Met Antibody 1.1. Production of "AbF46", a Mouse Antibody to c-Met 1.1.1 Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the first injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tail and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of phosphate buffered solution (PBS). The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in water at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (orthphenylenediamine; OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody was produced and purified from the cell culture.

First, the hybridoma cells cultured in 50 mL of a medium (DMEM) supplemented with 10% (v/v) fetal bovine serum (FBS) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mice antibody AbF46 produced in Reference Example 1.1 by replacing the constant region, but not the variable region responsible for antibody specificity, with an amino sequence of human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively, to construct a vector including the heavy chain and a vector including a light chain for the expression of the chimeric antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Thereafter, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, 100 mL of the supernatant was collected and applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest homology with the VH gene of the mouse antibody AbF46 purified in Reference Example 1.2 were analyzed. An Ig BLAST (www.ncbi.nlm nih.gov/igblast/) result revealed that VH3-71 has a homology of 83% at the amino acid level. CDR-H1, CDR-H2, and CDR-H3 of the mouse antibody AbF46 were defined according to Kabat numbering. A design was made to introduce the CDRs of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a search for BLAST. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest homology with the VH gene of the mouse antibody AbF46 were analyzed. An Ig BLAST (www.ncbi.nlm.nih.gov/igblast) search result revealed that VK4-1 has a homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest homology with the VL gene of the mouse antibody AbF46 were analyzed by a BLAST search (www.ncbi.nlm.nih.gov/igblast). As a result, VK2-40 was selected as well. VL and VK2-40 of the mouse antibody AbF46 were found to have a homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A BLAST search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy; SEQ ID NO: 47, H3-heavy; SEQ ID NO: 48, H4-heavy; SEQ ID NO: 49) and DNA fragments having the light chain nucleotide sequences (H1-light: SEQ ID NO: 50; H2-light: SEQ ID NO: 51; H3-light: SEQ ID NO: 52; H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) coding for the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDR and Synthesis of Primer The affinity maturation of huAbF46 was achieved. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides coding for heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed into tyrosine in all of the three antibodies to increase antibody production.

For use in constructing the three antibodies, (i) a polynucleotide (SEQ ID NO: 63) coding for a polypeptide (SEQ ID NO: 62) composed of the heavy chain variable region of huAbF46-H4-A1, a U6-HC7 hinge region, and a human IgG1 constant region, (ii) a polynucleotide (SEQ ID NO: 65) coding for a polypeptide (SEQ ID NO: 64) composed of the heavy chain variable region of huAbF46-H4-A1, a human IgG2 hinge region, and a human IgG1 region, (iii) a polynucleotide (SEQ ID NO: 67) coding for a polypeptide (SEQ ID NO: 66) composed of the heavy chain variable region of huAbF46-H4-A1, a human IgG2 region, and a human IgG2 constant region, and (iv) a polynucleotide (SEQ ID NO: 69) coding for a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (invitrogen) (A), and in another 15 ml tube, 100 μl of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1(U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the use in the following examples, and referred to as L3-1Y in the following examples.

Example 1

Preparation of Fusion Proteins

The anti-c-Met antibodies manufactured in Reference Example 1 were fused to a linker by coupling the C-terminal of their heavy chain therewith. Thereafter, an Ig2 domain, that is, amino acids from $129^{th}$ to $229^{th}$ among the amino acids constituting VEGF receptor 1 was sequentially fused at the terminal of the linker to manufacture antibodies capable of binding to c-Met and VEGF at the same time (see FIG. 1).

Among 1338 amino acids constituting VEGF receptor 1 (P17948.2; SEQ ID NO: 109), a gene sequence encoding 101 amino acids from $129^{th}$ to $229^{th}$ constituting the Ig2 domain which has been shown to be most important for VEGF-binding was secured from NCBI database.

```
Ig2 domain (VIG2) amino acid sequence (SEQ ID
NO: 110):
SDTGRPFVEMYSEIPEIIHMTEGRELVIPCRVTSPNITVTLKKFP

LDTLIPDGKRIIWDSRKGFIISNATYKEIGLLTCEATVNGHLYKT

NYLTHRQTNTI

Ig2 domain (VIG2) nucleotide sequence (SEQ ID
NO: 111):
AGTGATACAGGTAGACCTTTCGTAGAGATGTACAGTGAAATCCCC

GAAATTATACACATGACTGAAGGAAGGGAGCTCGTCATTCCCTGC

CGGGTTACGTCACCTAACATCACTGTTACTTTAAAAAAGTTTCCA
```

-continued

```
CTTGACACTTTGATCCCTGATGGAAAACGCATAATCTGGGACAGT

AGAAAGGGCTTCATCATATCAAATGCAACGTACAAAGAAATAGGG

CTTCTGACCTGTGAAGCAACAGTCAATGGGCATTTGTATAAGACA

AACTATCTCACACATCGACAAACCAATACAATC
```

In order to couple the heavy chain of the c-Met antibody manufactured in the above and the Ig2 domain (VIG2), three types of linkers were designed having repeating GGGGS motifs: 'GGGGS'(G4S), (SEQ ID NO: 116) 'GGGGSGGGGS'($(G4S)_2$) (SEQ ID NO: 117), or 'GGGGSGGGGSGGGGSGGGGS'($(G4S)_4$) (SEQ ID NO: 118). The peptide linker was to be placed between the c-Met antibody and the Ig2 domain (VIG2) of VEGF receptor 1. Accordingly, a gene was synthesized that encoded the heavy chain of the anti-c-Met antibody, the linker sequence, and the VEGF-binding fragment. The synthesized gene also included a stop codon (TGA) at the end of the designed final gene. The synthesized gene was inserted into pOptivec vector (Invitrogen) using an EcoRI/XhoI cloning site to produce a heavy chain expression vector. The vector used in the manufacture of L3-1Y was used as a light chain expression vector.

Each of the thus constructed vectors was amplified using Qiagen Maxiprep kit (Cat no. 12662), and the vector including the heavy chain and the vector containing the light chain were transfected at the ratio of 4:1 into 293T cells ($2.5\times10^7$ cells) to which 360 μl of 2 M $CaCl_2$ was added. Thereafter, the transfected cells were cultured in a DMEM medium containing 10% FBS at 37° C. in 5% $CO_2$ conditions for 5 hours, and then cultured in an FBS-free DMEM medium at 37° C. in 5% $CO_2$ conditions for 48 hours.

The cultured cells were centrifuged to obtain 100 ml of each supernatant, which was purified using AKTA Prime (GE Healthcare). Protein A column (GE Healthcare, 17-0405-03) was placed in the AKTA Prime, and the cultured solution flowed at a rate of 5 ml/min and was eluted with IgG elution buffer (Thermo Scientific, 21004). The buffer was exchanged with a PBS buffer, and thus antibodies capable of binding to cMet and VEGF at the same time were finally purified.

The thus prepared antibodies are summarized in Table 3:

TABLE 3

| | Name | Heavy Chain | Hinge | Constant Region | Linker | Light Chain | VEGF-binding fragment |
|---|---|---|---|---|---|---|---|
| Single-targeted antibody | L3-1 | SEQ ID NO: 62 | U6 HC7 (SEQ ID NO: 101) | IgG1 | — | SEQ ID NO: 70 | — |
| | L3-1Y | SEQ ID NO: 62 | U6 HC7 (SEQ ID NO: 101) | IgG1 | — | SEQ ID NO: 68 | — |
| Bispecific antibody | MV10A | SEQ ID NO: 62 | U6-HC7 (SEQ ID NO: 101) | IgG1 | (G4S)2 | SEQ ID NO: 70 | VIG2 (SEQ ID NO: 111) |
| | MV10AY | SEQ ID NO: 62 | U6-HC7 (SEQ ID NO: 101) | IgG1 | (G4S)2 | SEQ ID NO: 68 | VIG2 (SEQ ID NO: 111) |
| | MV10AY U3 HC9/ IgG1 | SEQ ID NO: 64 | U3 HC9 (SEQ ID NO: 102) | IgG1 | (G4S)2 | SEQ ID NO: 68 | VIG2 (SEQ ID NO: 111) |
| | MV10AY U3 HC9/ IgG2 | SEQ ID NO: 66 | U3 HC9 (SEQ ID NO: 102) | IgG2 | (G4S)2 | SEQ ID NO: 68 | VIG2 (SEQ ID NO: 111) |

Example 2 c-Met Target and Degradation Activity of Fusion Proteins 2.1. Affinity Test

The binding kinetics of the double-targeted fusion proteins manufactured in the above were analyzed using Biacore T100 instrument (GE Healthcare). A human Fab binding agent (GE Healthcare) was immobilized on the surface of a CM5 chip (GE Healthcare, Cat. No. BR-1005-30) according to the manufacturer's manual. About 90~120 RU of L3-1Y or MV10AY was captured and various concentrations of c-Met (R&D Systems, Cat. No. 358-MT/CF) were introduced to the captured antibodies by injection. Then, 10 mM Glycine-HCl (pH 1.5) solution was added thereto, whereby the surface was regenerated. In order to measure the binding kinetics, the data obtained from the above experiment was fitted using BIAevaluation software (GE Healthcare, Biacore T100 evaluation software).

The results obtained by using the BIAevaluation software are shown in Table 4 below.

TABLE 4

| Sample | $R_{max}$ (RU) | $K_D$ (nM) | $k_a$ (1/Ms) | $k_d$ (1/s) |
|---|---|---|---|---|
| L3-1Y | 89.63 | <0.01 | $7.7 \times 10^5$ | $<1.2 \times 10^{-5}$ |
| MV10AY | 89.59 | <0.01 | $6.8 \times 10^5$ | $<1.4 \times 10^{-5}$ |
| MV10AY U3 HC9/IgG2 | 102.5 | <0.01 | $7.2 \times 10^5$ | $<6.9 \times 10^{-5}$ |

The affinity of MV10AY toward c-Met was similar to that of L3-1Y ($K_D$<0.01 nM), regardless of the backbone isotype (IgG1 or IgG2) of the anti-c-Met antibodies.

2.2. c-Met Degradation ELISA (MKN45)

A relative total amount of c-Met was used to evaluate the effects of an antibody by figuring out the increase/decrease of the total amount of c-Met using the fact that the degradation of c-Met occurs by the internalization of the antibody when it binds to c-Met. It has been already shown that binding of c-Met to HGF promotes the growth of cancer cells and in this regard, the above experiment was created by the idea that if the total amount of c-Met is reduced, the growth of cancer cells decreases.

The amount of c-Met was measured by a quantitative ELISA method, and the experiment was performed in an MKN45 stomach cancer cell line (JCRB0254; Health Science Research Resource Bank (HSRRB, Shinjuku, Japan)), using human total HGF R/c-Met ELISA kit (R&D systems). Cells (200,000 cells/ml) were mixed with 5 μg/ml of anti-c-Met antibodies, and cultured in a medium (RPMI with 10% Fetal Bovine Serum) for 24 hours, followed by ELISA experiments. Lastly, they were reacted with Super Aquablue (eBiosciences) and their colorimetric signals were measured as OD values at the wavelength of 450 nm. The value of a control group (media) treated with no anti-c-Met antibody was set to 100%, and values obtained after treatment with the anti-c-Met antibodies were calculated as relative values against the control group.

Figure 2A:
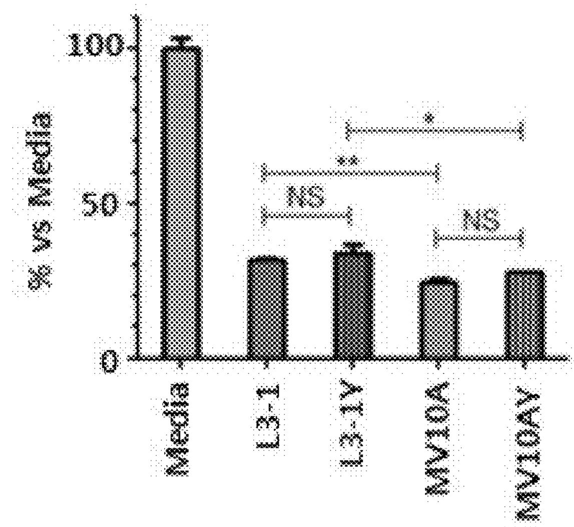
FIG. 2A is a graph showing the c-Met degradation activities of the bispecific antibodies prepared in one example. The value of a control group (media) treated with no anti-c-Met antibody was set to 100%. The values obtained after treatment with the anti-c-Met antibodies were calculated as relative values against the control group.

The obtained results are shown in FIG. 2A. As seen in FIG. 2A, MV10A and MV10AY, which are bispecific antibodies, had significantly improved c-Met degradation ability in comparison with L3-1 and L3-1Y each of which is the corresponding c-Met single-targeted antibody. That is, the c-Met degradation ability of MY10A (76%) was significantly improved in comparison with the degradation ability of its single-targeted antibody L3-1 (68%) (1-way ANOVA analysis result $p<0.01$). In the case of MV10AY, its degradation ability (72%) was also improved more than the degradation ability of its single-targeted antibody (66%) (1-way ANOVA analysis result $p<0.05$).

2.3. Akt Phosphorylation (Caki) (Agonism Test of Antibodies)

Safety and efficacy for therapeutic antibodies were evaluated by mechanism-based experiments. A phosphorylation degree of an AKT kinase was measured by the quantitative ELISA method so as to examine safety. Cellular activities controlled by AKT include cell proliferation, cell survival, cell size regulation, reactivity to soluble nutrients, intermediate metabolism, angiogenesis, tissue invasion, etc. All these processes represent the characteristics of cancer, numerous oncoproteins and tumor suppressors influence reciprocally to one another on the AKT route, and they perform to minutely regulate the cellular activities at a connection point of signal transduction and classic metabolic regulation. Accordingly, as the degree of a phosphorylated AKT which is an active form of AKT gets higher, cancer cells become more active. In this regard, this example investigated how much the antibodies could inhibit the phosphorylation of AKT, when compared to the treatment by the positive control antibody 5D5.

A site to be phosphorylated in AKT is Ser 473, and PathScan phospho-AKT1 (Ser473) chemiluminescent Sandwich ELISA kit from Cell signaling Co. was used. A Caki-1 kidney cancer cell line (HTB-46; American Type Culture Collection (ATCC), Manassas, Va.), which was cultured to 200,000 cells/ml one day before, was mixed with 5 μg/ml of antibodies in a serum-free DMEM medium (GIBCO, Invitrogen), and treated for 30 min., followed by experiments using an ELISA kit. The results were obtained by measuring with a machine of Perkins Elmer Co. When the phosphorylation degree of AKT was to be calculated, the phosphorylation degree of positive control 5D5 (American Type Culture Collection; ATCC, Manassas, Va.) was set to 100%. In comparison with this, the phosphorylation induction degrees of other anti-c-Met antibodies and bispecific antibodies were expressed.

Figure 2B:
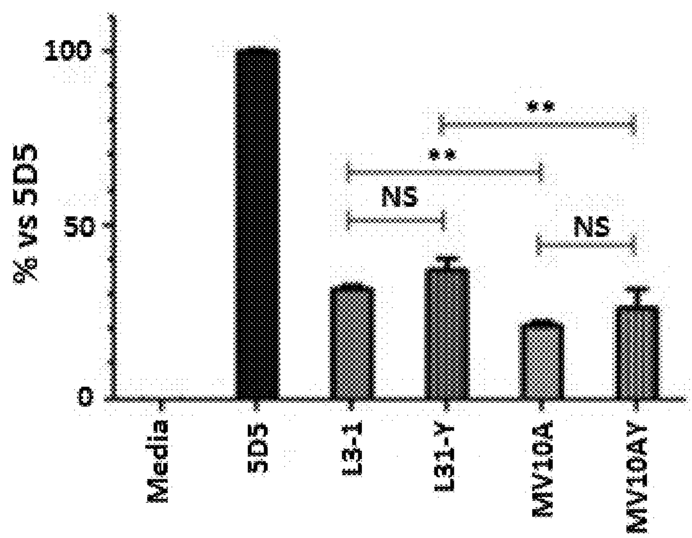
FIG. 2B is a graph showing the Akt phosphorylation inhibitory degrees of the bispecific antibodies prepared in one example. The value of a control group (5D5) was set to 100%.

The obtained results are shown in FIG. 2B. As seen in FIG. 2B, the bispecific antibodies (MV10A, MV10AY) inhibited the phosphorylation of AKT significantly more strongly than their corresponding c-Met single-targeted antibodies (L3-1, L3-1Y). That is, the AKT phosphorylation inhibitory ability of MV10A (79% compared to 5D5 control group) was significantly improved in comparison with the inhibitory ability (69%) of its single-targeted antibody L3-1 (1-way ANOVA analysis result $p<0.01$). In the case of MV10AY, its inhibitory ability (74%) was also improved more than the inhibitory ability (63%) of its single-targeted antibody L3-1Y (1-way ANOVA analysis result $p<0.01$).

2.4. MKN45 Growth Inhibition Test (Antibody Efficacy Test)

A human stomach cell line MKN45 (JCRB0254) was obtained from Health Science Research Resource Bank (HSRRB, Shinjuku, Japan). The cell line was cultured in an RPMI1640 medium (GIBCO, Cat. #11875-119) containing 10% (v/v) fetal bovine serum (FBS, GIBCO Cat. #16000-044) and 1% (v/v) penicillin/streptomycin (GIBCO, Cat. #15410-122). The cell line was cultured at 37° C. under a humid atmosphere containing 5% $CO_2$, and it was subcultured before confluence. The number of the cells was measured using CEDEX Analyzer (Roche Diagnostics). Luminescent assay by Celltiter Glo (CTG: Promega Co.) was employed to examine tumor cell proliferation according to in vitro antibody treatment.

The above assay was carried out according to the manufacturer's manual. In brief, the MKN45 cells within the RPMI1640 medium containing FBS 10% (v/v) were seeded at a concentration of $1\times10^4$ cells per well onto a black 96-well plate (Corning Incorporated, Cat. #Costar 3603), which was then treated with the antibodies of which the final concentrations were diluted to 0.008 μg/mL, 0.04 μg/mL, 0.2 μg/mL, and 1 μg/mL using a 10% FBS containing RPMI 1640 medium. After incubation for 72 hours, 100 microliter of CTG solution was added to each well, followed by incubation at a room temperature for 30 min. The obtained luminescent signals were recorded using Envision 2104 Multi-label Reader (Perkin Elmer, Waltham, Mass., USA).

Figure 2C:
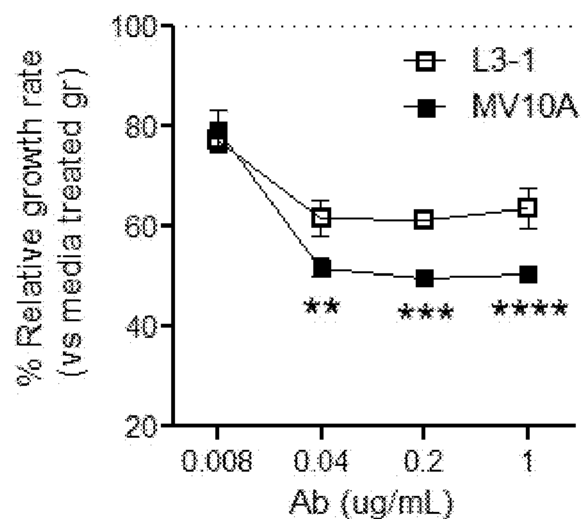
FIG. 2C is a graph showing the MKN45 cell line growth inhibitory degree of the bispecific antibody prepared in one example.

The obtained results are shown in FIG. 2C. As seen in FIG. 2C, bispecific antibody MV10A (■) showed significantly excellent MKN45 cancer cell line growth inhibitory effects at 0.04 μg/mL or higher concentrations in comparison with its corresponding c-Met single-targeted antibody L3-1 (□) (average and standard deviation marked, 2-way ANOVA analysis; p values obtained from Bonferroni multiple comparison test are marked below each concentration point. , p<0.01; *, p<0.001; ****, p<0.0001).

2.5. NCI-H441 Growth Test (Agonism Test of Antibodies)

When c-Met single-targeted antibody binds to c-Met, undesired agonism phenomenon by c-Met occurs. Since this is associated with the safety of the antibody, a test to evaluate whether the agonism properties which the c-Met single-targeted antibody does not want are not increased by having double target specificity was carried out using an NCI-H441 cell line. The NCI-H441 cell line has a tendency of cell division by agonism under specific conditions described below when administered with c-Met single-targeted antibody.

The NCI-H441 cell line (ATCC Cat. #HTB-174) was diluted at 200,000 cells/ml in a serum-free RPMI1640 medium (Gibco). seeded at 100 μl/well onto a 96 well plate, and then cultured at 37° C., in 5% $CO_2$ conditions for 24 hours. After that, they were treated with anti-c-Met antibodies having 6 concentration gradients in ⅕ serial dilution starting from the concentration of 10 μg/ml. After the cells were cultured at 37° C., in 5% $CO_2$ conditions for 21 hours, 5-bromo-2'-deoxyuridine (BrdU) was added to be incorporated into the cells, which were further cultured for 3 hours, followed by BrdU assay (Roche, Indianapolis, Ind.). The cells were subjected to denaturation/fixation on a plate, anti-BrdU antibodies were added thereto, a substrate was added 1 hour thereafter, and a color reaction was measured using an ELISA spectraMax reader (Molecular Devices, Sunnyvale, Calif.). Lastly, after the subtraction of the value of cells into which BrdU was not incorporated as a background control, the value of a control group to which no anti-c-Met antibodies were treated was converted to 100% (Y axis) to calculate relative values. Mouse IgG was used as a negative control and a 5D5 antibody (isolated and purified from ATCC Cat. #HB11895 hybridoma cells) known to be an agonist was used as a positive control.

Figure 2D:
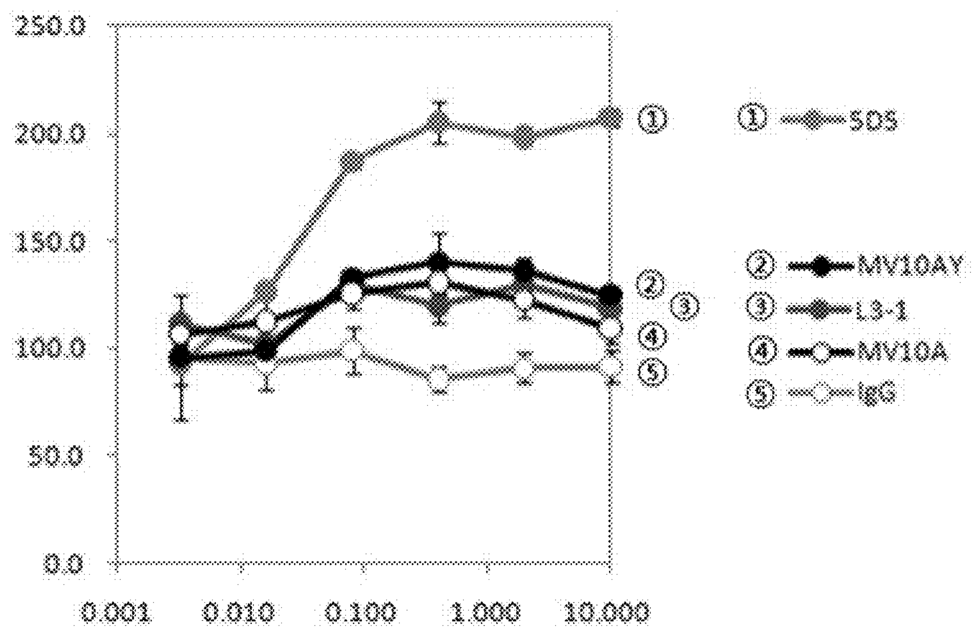
FIG. 2D is a graph showing the NCI-H441 cell line growth inhibitory degrees of the bispecific antibodies prepared in one example.

The obtained results are shown in FIG. 2D. As seen in FIG. 2D, the bispecific antibody MV10A or MV10AY did not increase agonism properties when compared to the c-Met single-targeted antibody L3-1. In other words, there were no changes in antibody safety.

2.6. HUVEC Proliferation Suppression Test (+HGF) (Anti-Angiogenesis Test)

A HuVEC cell line (ATCC) was cultured along with 0.4 μg/ml of HGF (R&D systems) in an EGM2 bulletkit medium (Lonza Cat. CC-3162). After the cells were incubated under a humid atmosphere containing 5% $CO_2$ at 37° C., they were subcultured before confluence. The number of the cells was measured using a CEDEX Analyzer (Roche Diagnostics). Real time cell analysis was conducted using Xcelligence Real time cell analyzer (Roche) in order to see tumor cell growth inhibition degree according to in vitro antibody treatment. This analysis was carried out according to the manufacturer's manual. In brief, the cultured HuVEC cells were seeded at a concentration of $1\times10^4$ cells per well onto a 16-well E-plate, the incubated medium was removed after 24 hours, and the cells were treated with an antibody (100 μl, final antibody concentration 10 μg/mL) which was diluted in a free-serum medium (EBM media, Lonza Co.). The values of occurring impedances were measured at real time. Real time analysis was conducted for 48 hours.

Figure 2E:
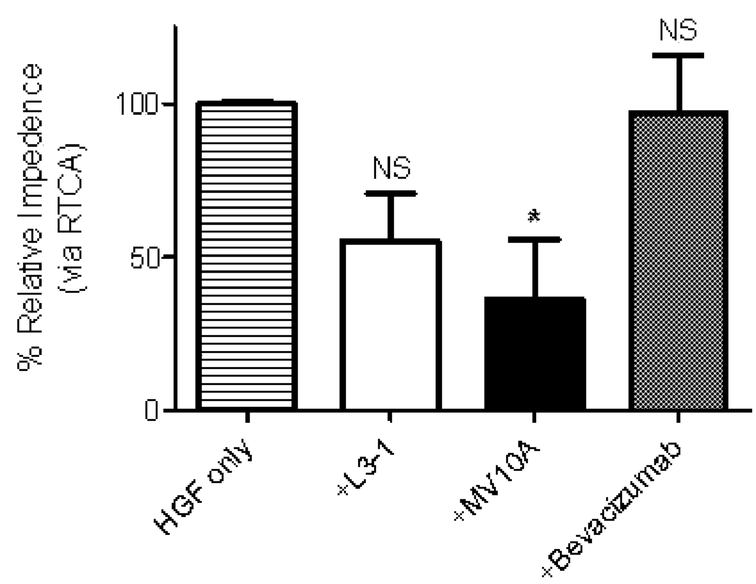
FIG. 2E is a graph showing the HUVEC proliferation inhibitory degree of the bispecific antibody prepared in one example when HGF is added.

The obtained results are shown in FIG. 2E. By virtue of these test results, it could be determined how much the single/bispecific antibodies could suppress the influence of HGF on the growth of HUVEC. As seen in FIG. 2E, Bevacizumab (Roche Korea, the same amount treated) did not have any influences on the effects of HGF, like the negative control (HGF only). Nonetheless, MV10A, the bispecific antibody of c-Met and VEGFR, showed stronger agonism effects on HGF than its original c-Met single-targeted antibody, L3-1 (MV10A 64% suppression, L3-1 45% suppression; compared to HGF only group, p value marked by 1-way ANOVA: *, p<0.05; NS, no significance).

Example 3

VEGF Target and Suppression Activity of Fusion Proteins 3.1. Affinity Test

The binding kinetics of the double-specific antibodies having VEGF as a target were measured by an SPR method using Biacore T100 instrument (GE Healthcare). hVEGF (GE Healthcare, 28-9583-25) was immobilized on the surface of a CM5 chip according to the manufacturer's manual. MV10AY having various concentrations (6 types of concentrations) of about 90 RU was captured. The obtained surface was regenerated by injecting 1M NaCl+30 mM NaOH at a fluid rate of 30 μl/min for 60 sec. In order to determine binding kinetics, the data obtained from the above experiment was fitted using BIAevaluation software (GE Healthcare) ($K_{D=}$=0.45 nM).

The obtained results are shown in Table 5.

TABLE 5

| Sample | $R_{max}$ (RU) | $K_D$ (nM) | $k_a$ (1/Ms) | $k_d$ (1/s) |
|---|---|---|---|---|
| MV10AY | 92.30 | 0.45 | $2.4 \times 0^6$ | $1.1 \times 0^{-3}$ |

3.2. HUVEC Proliferation Suppression Test (+VEGF)

Anti-angiogenesis effects were examined by investigating HUVEC proliferation degree according to in vitro antibody treatment using Xcelligence Real time cell analyzer (Roche). The analysis was carried out according to the manufacturer's manual. In brief, a HuVEC cell line (ATCC) was cultured along with 0.4 μg/ml of VEGF (R&D systems) in an EGM2 bulletkit medium (Lonza Cat. CC-3162). The cultured HuVEC cells were seeded at a concentration of $1\times10^4$ cells per well onto a 16-well E-plate, the incubated medium was removed after 24 hours, and the cells were treated with the antibodies (100 μl, final concentration 10 μg/mL) which were diluted in a free-serum medium (EBM media, Lonza). The values of occurring impedances were measured at real time. Real time analysis was conducted for 96 hours.

Figure 3A:
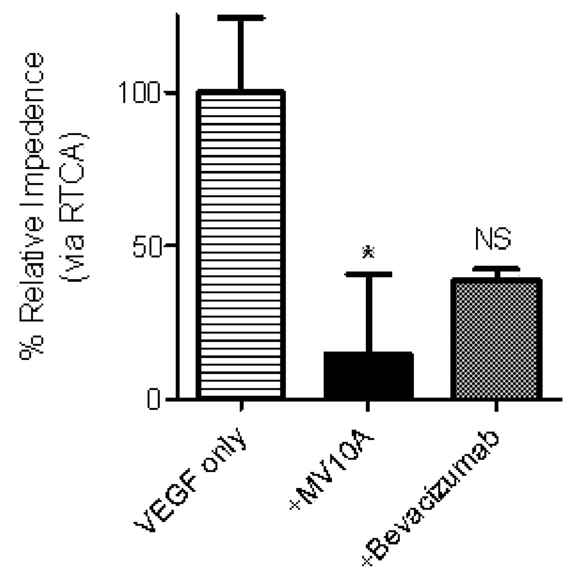
FIG. 3A is a graph showing HUVEC proliferation inhibitory degree of the bispecific antibody prepared in one example when VEGF is added.

The obtained results are shown in FIG. 3A. As seen in FIG. 3A, the antibody according to the invention and Bevacizumab (Roche Korea, the same amount treated) used as a positive control all showed VEGF-dependent cell proliferation, and MV10A showed significant cell proliferation suppression effects, compared to its positive control, Bevacizumab (MV10A 86% suppression, Bevacizumab 61% suppression; compared to VEGF only group, p value marked by 1-way ANOVA: *, p<0.05; NS, no significance).

3.3. HUVEC Proliferation Suppression Test (+VEGF+HGF)

Anti-angiogenesis effects were examined by investigating HUVEC proliferation degree according to in vitro antibody treatment using Xcelligence Real time cell analyzer (Roche). The analysis was carried out according to the manufacturer's manual. In brief, cells (HuVEC, ATCC, 10000 cells/well) were treated with 0.4 μg/ml of VEGF (R&D systems) which is a ligand of c-Met and VEGFR and cultured in an EGM2 bulletkit medium (Lonza Cat. CC-3162). The cultured HuVEC cells were seeded at a concentration of $1\times10^4$ cells per well onto a 16-well E-plate, the incubated medium was removed after 24 hours, and the cells were treated with the antibodies (100 μl, final concentration 10 μg/mL) which were diluted in a free-serum medium (EBM media, Lonza). The values of occurring impedances were measured at real time. Real time analysis was conducted for 48 hours.

Figure 3B:
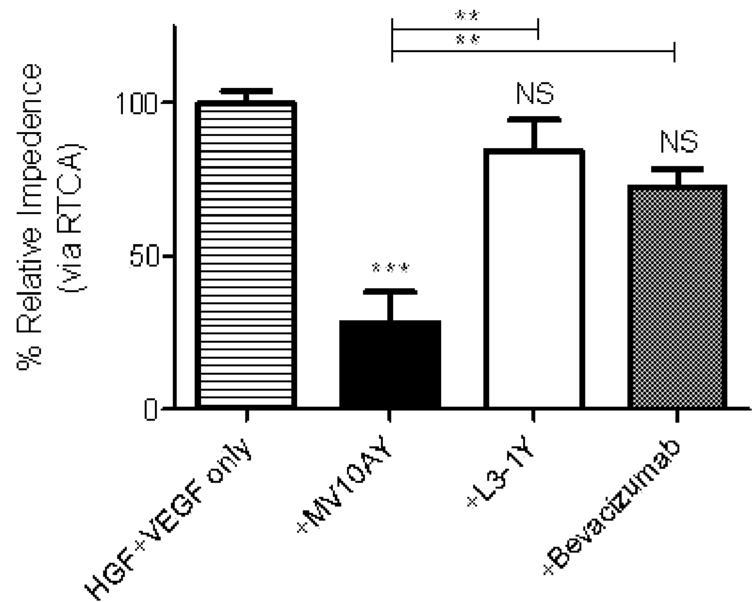
FIG. 3B is a graph showing the HUVEC proliferation inhibitory degree of the bispecific antibody prepared in one example when VEGF+HGF are added.

The obtained results are shown in FIG. 3B. As seen in FIG. 3B, while the single administration of the single-targeted (c-Met) antibody L3-1Y and Bevacizumab (VEGF single target) antibody did not result in any significant HuVEC cell proliferation suppression effects, the bispecific antibody MV10AY showed significant synergistic suppression effects against HGF- and VEGF-dependent HUVEC cell proliferation. In other words, while the sole use of Bevacizumab showed 27% suppression and the sole use of L3-1Y showed only 16% suppression, the double-targeted MV10A antibody showed 72% suppression effects. Thus, when the bispecific antibody was used, the significant synergistic suppression effects were observed, compared to when the single antibodies were used (significance marked by 1-way ANOVA test with Bonferonni multiple comparison test. compared to HGF+VEGF only group at the top of the bar graph p value marked (***, $p<0.001$; NS, no significance), differences between each treatment group marked at the top of the graph).

3.4. HUVEC Invasion Inhibition Test (+VEGF)

In order to see whether in vitro antibody treatment inhibits cell invasion, the cell invasion was tested using a plate for cell invasion assay (BioCoat Growth Factor Reduced MATRIGEL Invasion Chamber; BD science, Cat#. 354483) which is divided into an upper chamber and a lower chamber and the upper chamber of which is coated with collagen. The assay was carried out according to the manufacturer's manual. In brief, HUVEC cells (ATCC; $5\times10^4$ cells/well) were seeded into the upper chamber, and the lower chamber was treated with the antibody (10 μg/ml), which was then cultured at 37° C. (VEGF added to the lower chamber, 0.4 μg/ml). After 24 hours, the cells which went down to the lower chamber by penetrating the collagen layer of the upper chamber were dyed with calcein and observed using a fluorescence spectroscopy (ZEISS).

Figure 3C:
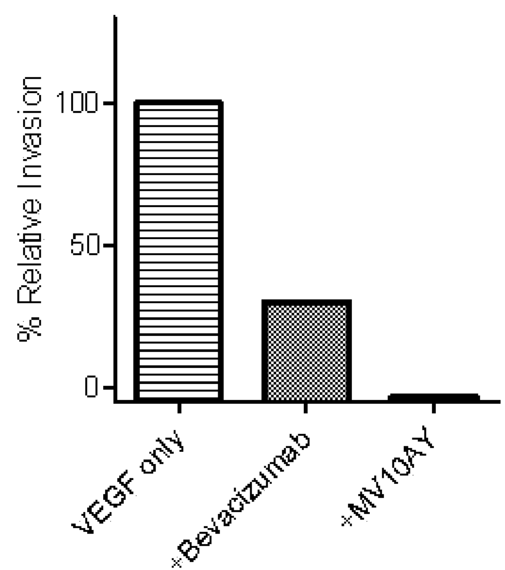
FIG. 3C is a graph showing relative invasion (upper portion) and contains photographs (lower portion).
Figure 3C:
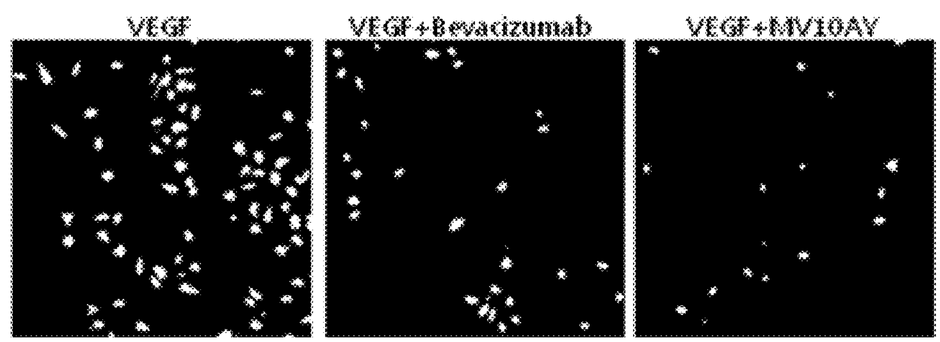

The obtained results and the fluorescence images are shown in FIG. 3C. The upper portion of FIG. 3C is a graph showing the relative fluorescence image areas of each antibody treatment group. They are relative values against the invasion occurring when treated with VEGF only (100%). The lower portion of FIG. 3C contains photographs illustrating actual fluorescence images (white indicates the cells which caused invasion). As seen in FIG. 3C, the double-specific antibody MV10AY showed significant invasion suppression effects in comparison with Bevacizumab, the VEGF single-targeted antibody (MV10AY 100% suppression, Bevacizumab 70% suppression).

3.5. HUVEC Invasion Inhibition Test (+VEGF+HGF)

In order to see whether in vitro antibody treatment inhibits cell invasion, the cell invasion was tested using a plate for cell invasion ability assay (BioCoat Growth Factor Reduced MATRIGEL Invasion Chamber; BD science, Cat#. 354483) which is divided into an upper chamber and a lower chamber and the upper chamber of which is coated with collagen. The assay was carried out according to the manufacturer's manual.

In brief, HUVEC cells (ATCC; $5\times10^4$ cells/well) were seeded into the upper chamber, and the lower chamber was treated with the antibody (10 μg/ml), which was then cultured at 37° C. (HGF+VEGF added to the lower chamber, 0.4 μg/ml each). After 24 hours, the cells which went down to the lower chamber by penetrating the collagen layer of the upper chamber were dyed with calcein and observed using a fluorescence spectroscopy (ZEISS).

Figure 3D:
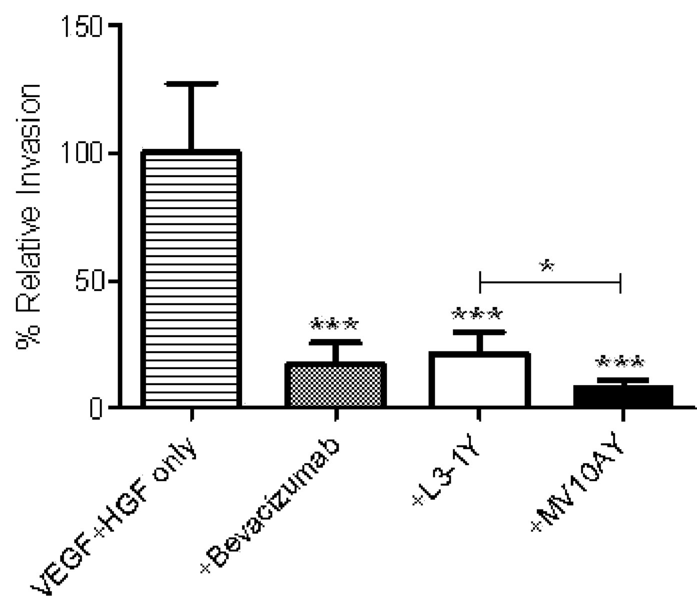
FIG. 3D is a graph showing the HUVEC invasion inhibitory degree of the bispecific antibody prepared in one example when VEGF+HGF are added. The upper portion is a graph showing the relative fluorescence image areas of each treatment group. The lower portion contains photographs illustrating fluorescence images with each of the identified antibodies
Figure 3D:
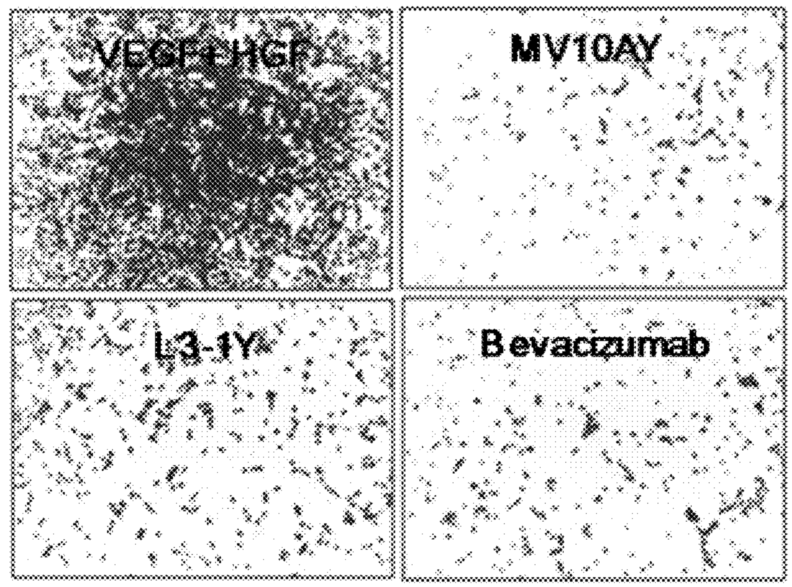
Figure 3E:
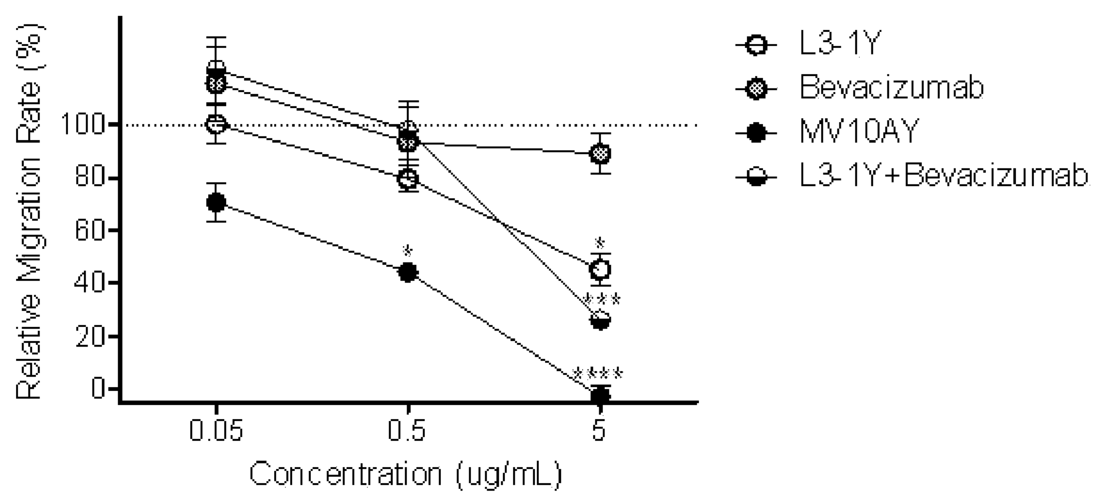
FIG. 3E is a graph showing the cell migration inhibitory degree of the bispecific antibody prepared in one example.

The obtained results and the fluorescence images are shown in FIG. 3D. The upper portion of FIG. 3D is a graph showing the relative fluorescence image areas of each antibody treatment group. They are relative values against the invasion occurring when treated with VEGF+HGF (100%). As the values go lower, it means that less invasion occurs. The averages and standard deviations are marked, and p values with regard to VEGF+HGF treatment group as a result of 1-way ANOVA analysis are each marked at the top of the graph (*, $p<0.05$; *, $p<0.001$). The lower portion of FIG. 3D contains photographs illustrating actual fluorescence images (black indicates the cells which caused invasion). As seen in FIG. 3**D, the double-specific antibody MV10AY showed remarkably excellent inhibitory effects against HuVEC cell invasion in the presence of VEGF and HGF in comparison with L3-1Y antibody, the c-Met single-targeted antibody (MV10AY 92% suppression; L3-1Y 79% suppression; and Bevacizumab 83% suppression).

3.6. HUVEC Migration Inhibition Test (+VEGF+HGF)

Both c-Met and VEGF are factors associated with not only cell growth but also cancer metastasis. It was tested whether the bispecific antibody has synergistic effects on cell migration related to cancer cell metastatic potential. To evaluate metastatic potential inhibition according to in vitro antibody treatment, the following experiments were carried out. Since cell migration is directly involved in the metastasis of cancers, the following analysis is commonly used to evaluate cell metastatic potential.

Oris 96-well plate (Platypus, Oris™ Cell migration assay) method was performed. HuVEC cells (ATCC) were seeded at 10000 per well onto a 96-well plate equipped with a stopper and treated with 0.4 μg/ml of HGF and 0.4 μg/ml of VEGF in a serum-free medium (EBM, Lonza). Then, after culturing for 24 hours, the stoppers were removed. Because the stopper is a circular rubber material, which prevents cells from growing at a place where the stopper was once placed, the removal of the stopper after 24 hours would result in a circular space at only that place.

After the removal of the stoppers, the cells were treated with anti-c-Met antibody L3-1Y, anti-VEGF antibody Bevacizumab, and MV10AY antibody at various concentrations (0.05 to 5 μg/ml). Then, after 24 hours, they were dyed with calcein AM (BD) which is a fluorescent substance, so that only the cells were dyed and the portions with no cells remained as spaces. Hence, as cell migration is inhibited more, the size of the space which is not dyed will get bigger and in this regard, cell migration degree can be measured by observing the space which is not dyed. The strength of fluorescence signals was read by a multilabel reader (PerkinElmer, Envision), and the obtained values were converted on the basis of the signal strength (100%) of VEGF+HGF treatment group and shown in FIG. 3E. The average and standard deviation at each concentration are shown, and their statistic significances with regard to VEGF+HGF group were marked at the top of each concentration point (2-way ANOVA with Bonferonni multiple comparison test; * $p<0.05$; * $p<0.001$; ** $p<0.0001$).

At the treatment amounts of the antibodies within all the tested ranges, the bispecific antibody MV10AY showed remarkably excellent inhibitory effects, compared to the treatment of the c-Met single-targeted antibody (L3-1Y) or the VEGF single-targeted antibody Bevacizumab or the co-treatment of these single-targeted antibodies (synergism observed). This result undoubtedly shows the superiority of the MV10AY antibody which is an anti-c-Met antibody with added anti-VEGF function.

Example 4

In Vivo Anticancer Effects of Fusion Proteins

In vivo anticancer effects were tested using a U87-MG brain cancer cell line known to have anticancer effects when c-Met/HGF and VEGF are each suppressed. $2.5\times10^6$ (100 μl) of the U87-MG brain cancer cell line (purchased from cell bank of Chinese Academy of Sciences; ATCC catalog no. HTB-14) were subcutaneously injected into BALB/c Nude mice (males, 6-7 weeks, 20-25 grams). After 1 week passed, the mice were divided into two groups: treatment groups as illustrated in FIG. 4A (MV10AY (■), MV10AY U3 HC9/IgG1 (□), or MV10AY U3 HC9/IgG2 (○); administration amount: 0.2 mg/kg each (dotted line) or 1 mg/kg (solid line); administration time: every 3-4 days or 10 days; administration route: intravenous injection) and control group (vehicle: PBS 0.2 mL administered by intravenous injection once a week), followed by drug administration. There were 15 mice in each group. Tumor volumes were measured twice a week, and the tumor volumes were calculated as {long diameter (mm)×short diameter $(mm)^2$}/2. After 30 days from the treatment, the mice were euthanized, the tumors were extracted therefrom, and the weights of the tumors were measured and then used for the evaluation of anticancer effects along with the tumor volumes measured in the above.

The obtained results are shown in FIG. 4A. The upper portion of FIG. 4A is a graph illustrating tumor volumes according to time, and the bottom portion of FIG. 4A is a graph illustrating the weights of the tumors that were extracted after the completion of the experiment. As seen in FIG. 4A, all the treatment groups showed remarkable tumor inhibitory effects after two weeks from the administration. Treatment effect differences among the three bispecific antibodies were not significant, and the groups in which the administration amounts and administration intervals were increased showed much stronger inhibitory effects. The groups in which 1 mg/kg was injected every 3-4 days showed almost perfect anticancer effects to such an extent that tumors were hardly observed (top graph repeated measures ANOVA analysis,  ($p<0.01$),  ($p<0.0001$); bottom graph 1-way ANOVA Dunnett's multiple comparison test analysis with regard to the Vehicle group,  ($p<0.01$), *** ($p<0.0001$)).

In order to see whether the bispecific antibody that targets c-Met and VEGF at the same time shows more improved anticancer effects than the c-Met single-targeted antibody, an in vivo anticancer effect experiment was conducted using a NCI-H441 cell line. NCI-H441 is a cell line which shows anticancer effects as well as agonism effects by virtue of a c-Met target, and was determined to be the most suitable cell line to see comprehensive anticancer effects. $5\times10^6$ (100 μl) of the NCI-H441 lung cancer cell line (purchased from ATCC, Cat. #HTB-174) were subcutaneously injected into BALB/c Nude mice (males, 5-6 weeks, 20-25 g). After 1 week passed, the mice were divided into two groups: treatment groups (single-targeted antibody L3-1Y and bispecific antibody 5 mg/kg each, administered once a week) and a control group (vehicle: PBS 0.2 mL administered by intravenous injection once a week), followed by drug administration. There were 15 mice in each group. Tumor volumes were measured twice a week, and the tumor volumes were calculated as {long diameter (mm)×short diameter $(mm)^2$}/2. After 26 days from the start of the treatment, the mice were euthanized, the tumors were extracted therefrom, and the weights of the tumors were measured and then used for the evaluation of anticancer effects along with the tumor volumes measured in the above.

Figure 4B:
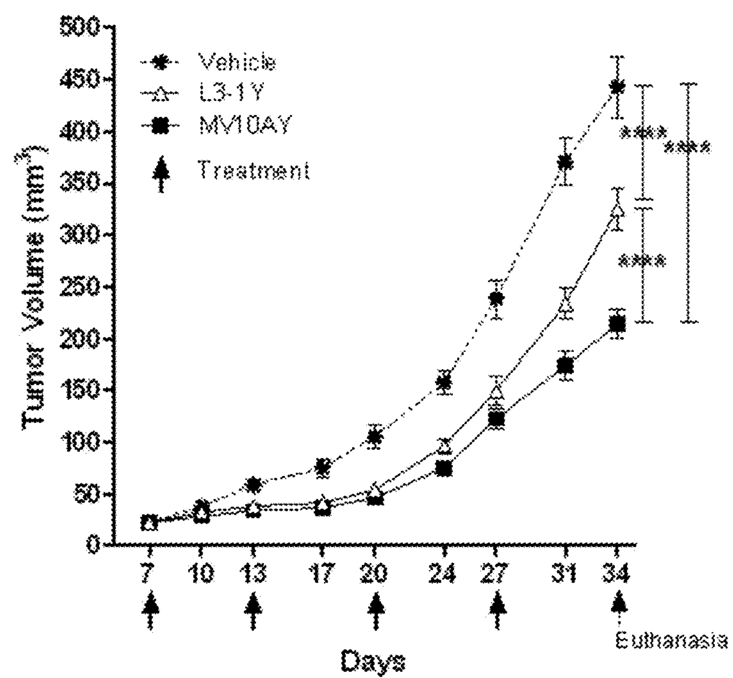
FIG. 4B illustrates the in vivo anticancer effects of the bispecific antibody prepared in one example against NCI-H441 lung cancer cells. The upper portion of FIG. 4B is a graph illustrating tumor volumes according to time. The lower portion is a graph illustrating the weights of tumors that were extracted after completion of treatment.
Figure 4B:
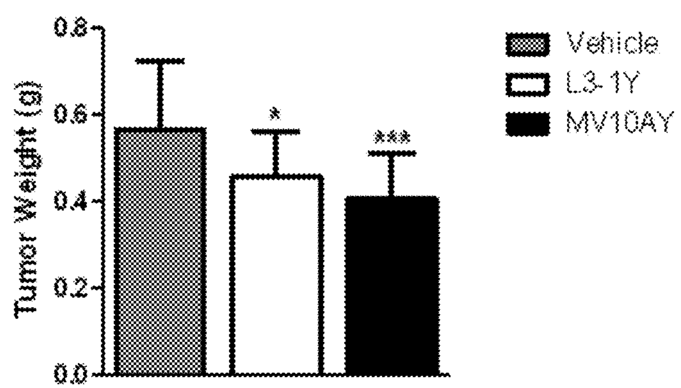

The obtained results are shown in FIG. 4B. The upper portion of FIG. 4B is a graph illustrating tumor volumes according to time, and the lower portion of FIG. 4B is a graph illustrating the weights of the tumors that were extracted after the completion of the experiment. As seen in FIG. 4B, statistically significant anticancer effects were observed after one week from the start of administration in both of the two treatment groups. Especially, when treated with MV10AY, stronger anticancer effects were observed than when treated with L3-1Y (top graph repeated measures ANOVA analysis, **** ($p<0.0001$); bottom graph 1-way ANOVA with Dunnett's multiple comparison test analysis vs the Vehicle group, * ($p<0.05$), *** ($p<0.0001$)).

Example 5

Fusion Proteins Comprising Various Anti-c-Met Antibodies

It was examined whether the efficacy of anti-c-Met antibodies having other CDRs (in addition to L3-1, L3-1Y, or L3-1Y IgG2 which were illustrated in the above examples) is improved when fused with VIG2.

The efficacy of the anti-c-Met antibodies was measured by testing c-Met degradation degree according to the same method as described in Example 2.2, and the antibodies used are summarized in Table 6 below.

TABLE 6

| Name | Heavy Chain | Light Chain | Linker | VEGF-binding fragment |
|---|---|---|---|---|
| Ab1 | SEQ ID NO: 112 | SEQ ID NO: 113 | — | — |
| Ab1-VIG2 | SEQ ID NO: 112 | SEQ ID NO: 112 | $(G4S)_2$ | VIG2 (SEQ ID NO: 110) |
| Ab2 | SEQ ID NO: 114 | SEQ ID NO: 115 | — | — |
| Ab2-VIG2 | SEQ ID NO: 114 | SEQ ID NO: 115 | $(G4S)_2$ | VIG2 (SEQ ID NO: 110) |

Figure 5:
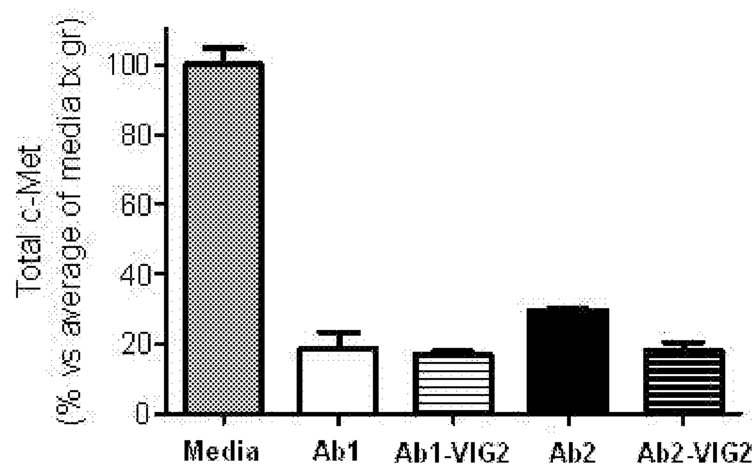
FIG. 5 is a graph showing the comparison of the c-Met degradation activities of various c-Met antibodies fused with VIG2 according to one example with that of c-Met antibody with no VIG2.

The obtained results are shown in FIG. 5. As seen in FIG. 5, the bispecific antibodies, Ab1-VIG2 and Ab2-VIG2 improved c-Met degradation ability compared to their c-Met single-targeted antibodies Ab1 and Ab2, respectively. That is, the c-Met degradation ability (83.2%) of Ab1-VIG2 was improved in comparison with the degradation ability (81.7%) of its single-targeted antibody Ab1. In the case of Ab2-VIG2, its degradation ability (81.9%) was improved more than the degradation ability (70.4%) of its single-targeted antibody Ab2 (t-test analysis result $p<0.01$).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fusion protein comprising (a) an anti-c-Met antibody or an antigen-binding fragment of the anti-c-Met antibody, wherein the anti-c-Met antibody specifically binds to an epitope comprising 5 to 19 contiguous amino acids of SEQ ID NO: 71, and wherein the epitope comprises the amino acid sequence of SEQ ID NO: 73, and (b) a VEGF-binding polypeptide, wherein the VEGF-binding polypeptide is an anti-VEGF antibody or antigen-binding fragment thereof, or a VEGF receptor or VEGF-binding region thereof.

2. The fusion protein according to claim 1, wherein the VEGF-binding polypeptide is a VEGF receptor comprising SEQ ID NO: 109 or a polypeptide comprising 102 to 1338 consecutive amino acids of SEQ ID NO: 109 comprising SEQ ID NO: 110.

3. The fusion protein according to claim 1, further comprising a linker between (a) the anti-c-Met antibody or the antigen-binding fragment of the anti-c-Met antibody and (b) the VEGF-binding polypeptide.

4. The fusion protein according to claim 3, wherein the linker is a peptide linker comprising 1 to 100 amino acids.

5. The fusion protein according to claim 1, wherein the anti-c-Met antibody comprises:

a heavy chain variable region comprising (a) a heavy chain complementarity determining region H1 (CDR-H1) comprising the amino acid sequence of SEQ ID NO: 4; (b) a CDR-H2 comprising the amino acid sequence of SEQ ID NO: 5 or SEQ ID NO: 2; and (c) a CDR-H3 comprising the amino acid sequence of SEQ ID NO: 3 or SEQ ID NO: 6; and a light chain variable region comprising (a) a light chain complementarity determining region L1 (CDR-L1) comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9 or SEQ ID NO: 15.

6. The fusion protein according to claim 5, wherein the CDR-H1 has the amino acid sequence of SEQ ID NO: 1, SEQ ID NO: 22, SEQ ID NO: 23, or SEQ ID NO: 24, the CDR-H2 has the amino acid sequence of SEQ ID NO: 2, SEQ ID NO: 25, or SEQ ID NO: 26, the CDR-H3 has the amino acid sequence of SEQ ID NO: 3, SEQ ID NO: 27, SEQ ID NO: 28, or SEQ ID NO: 85, the CDR-L1 has the amino acid sequence of SEQ ID NO: 10, SEQ ID NO: 29, SEQ ID NO: 30, SEQ ID NO: 31, SEQ ID NO: 32, SEQ ID NO: 33, or SEQ ID NO: 106, the CDR-L2 has the amino acid sequence of SEQ ID NO: 11, SEQ ID NO: 34, SEQ ID NO: 35, or SEQ ID NO: 36, and the CDR-L3 has the amino acid sequence of SEQ ID NO: 12, SEQ ID NO: 13, SEQ ID NO: 14, SEQ ID NO: 15, SEQ ID NO: 16, SEQ ID NO: 37, SEQ ID NO: 86, or SEQ ID NO: 89.

7. The fusion protein according to claim 5, wherein the heavy chain variable region comprises the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94, and the light chain variable region comprises the amino acid sequence of SEQ ID NO: 119 SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107.

8. The fusion protein according to claim 5, wherein the anti-c-Met antibody comprises:

a heavy chain comprising the amino acid sequence of SEQ ID NO: 62, the amino acid sequence from the 18$^{th}$ to 462$^{nd}$ positions of SEQ ID NO: 62, the amino acid sequence of SEQ ID NO: 64, the amino acid sequence from the 18$^{th}$ to 461$^{st}$ positions of SEQ ID NO: 64, the amino acid sequence of SEQ ID NO: 66, or the amino acid sequence from the $18^{th}$ to $460^{th}$ positions of SEQ ID NO: 66; and a light chain comprising the amino acid sequence of SEQ ID NO: 68, the amino acid sequence from the $21^{st}$ to $240^{th}$ positions of SEQ ID NO: 68, the amino acid sequence of SEQ ID NO: 70, the amino acid sequence from the $21^{st}$ to $240^{th}$ positions of SEQ ID NO: 70, or the amino acid sequence of SEQ ID NO: 108.

9. The fusion protein according to claim 1, wherein the anti-c-Met antibody is a monoclonal antibody.

10. The fusion protein according to claim 1, wherein the anti-c-Met antibody is a mouse originated antibody, a mouse-human chimeric antibody, a humanized antibody, or a human antibody.

11. The fusion protein according to claim 1, wherein the fusion protein comprises an antigen-binding fragment of an anti-c-Met antibody selected from the group consisting of scFv, $(scFv)_2$, Fab, Fab', and $F(ab')_2$.

12. A bispecific antibody against c-Met and VEGF, comprising the fusion protein of claim 1.

13. A method of treating a disease induced by c-Met or VEGF, comprise administering a pharmaceutical amount of the bispecific antibody of claim 12 to a patient in need thereof, thereby treating a disease induced by c-Met or VEGF in the patient, wherein the disease is a cancer, gestational diabetes, diabetic retinopathy, or macular degeneration.

14. A method of preparing a fusion protein according to claim 1 comprising expressing a nucleic acid encoding the fusion protein in a cell.

15. A fusion protein comprising (a) an anti-c-Met antibody or an antigen-binding fragment of the anti-c-Met antibody, wherein the anti-c-Met antibody comprises a heavy chain comprising the amino acid sequence of SEQ ID NO: 112 or SEQ ID NO: 114; and a light chain comprising the amino acid sequence of SEQ ID NO: 113 or SEQ ID NO: 115, and (b) a VEGF-binding polypeptide, wherein the VEGF-binding polypeptide is an anti-VEGF antibody or antigen-binding fragment thereof, or a VEGF receptor or VEGF-binding region thereof.

16. A method of preparing an anti-c-Met antibody having improved efficacy, comprising coupling an anti-c-Met antibody or an antigen-binding fragment of the antibody, with a VEGF-binding polypeptide, wherein the VEGF-binding polypeptide comprises SEQ ID NO: 110, or 102 to 1338 consecutive amino acids of the amino acid sequence of SEQ ID NO: 109 and comprising the amino acid sequence of SEQ ID NO: 110.

17. The method according to claim 16, wherein the VEGF-binding polypeptide is coupled to the anti-c-Met antibody or an antigen-binding fragment thereof through a linker.

* * * * *

SEQUENCE LISTING

```
<160> NUMBER OF SEQ ID NOS: 119

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5


<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly


<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5


<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
```

```
<220> FEATURE:
<221> NAME/KEY: UNSURE
<222> LOCATION: (1)..(1)
<223> OTHER INFORMATION: X is Pro or Ser or absent
<220> FEATURE:
<221> NAME/KEY: UNSURE
<222> LOCATION: (2)..(2)
<223> OTHER INFORMATION: X is Glu or Asp

<400> SEQUENCE: 4

Xaa Xaa Tyr Tyr Met Ser
1               5


<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: UNSURE
<222> LOCATION: (3)..(3)
<223> OTHER INFORMATION: X is Asn or Lys
<220> FEATURE:
<221> NAME/KEY: UNSURE
<222> LOCATION: (4)..(4)
<223> OTHER INFORMATION: X is Ala or Val
<220> FEATURE:
<221> NAME/KEY: UNSURE
<222> LOCATION: (7)..(7)
<223> OTHER INFORMATION: X is Asn or Thr

<400> SEQUENCE: 5

Arg Asn Xaa Xaa Asn Gly Xaa Thr
1               5


<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: UNSURE
<222> LOCATION: (5)..(5)
<223> OTHER INFORMATION: X is Ser or Thr

<400> SEQUENCE: 6

Asp Asn Trp Leu Xaa Tyr
1               5


<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: UNSURE
<222> LOCATION: (4)..(4)
<223> OTHER INFORMATION: X is His, Arg, Gln or Lys
<220> FEATURE:
<221> NAME/KEY: UNSURE
<222> LOCATION: (12)..(12)
<223> OTHER INFORMATION: X is His or Gln
<220> FEATURE:
<221> NAME/KEY: UNSURE
<222> LOCATION: (13)..(13)
<223> OTHER INFORMATION: X is Lys or Asn
<220> FEATURE:
<221> NAME/KEY: UNSURE
<222> LOCATION: (9)..(9)
<223> OTHER INFORMATION: X is Ser or Trp
```

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: UNSURE
<222> LOCATION: (2)..(2)
<223> OTHER INFORMATION: X is Ala or Gly
<220> FEATURE:
<221> NAME/KEY: UNSURE
<222> LOCATION: (4)..(4)
<223> OTHER INFORMATION: X is Thr or Lys
<220> FEATURE:
<221> NAME/KEY: UNSURE
<222> LOCATION: (7)..(7)
<223> OTHER INFORMATION: X is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: UNSURE
<222> LOCATION: (1)..(1)
<223> OTHER INFORMATION: X is Gly, Ala or Gln
<220> FEATURE:
<221> NAME/KEY: UNSURE
<222> LOCATION: (6)..(6)
<223> OTHER INFORMATION: X is Arg, His, Ser, Ala, Gly or Lys
<220> FEATURE:
<221> NAME/KEY: UNSURE
<222> LOCATION: (8)..(8)
<223> OTHER INFORMATION: X is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:

<223> OTHER INFORMATION: Synthetic (light chain CDR2 of AbF46)

<400> SEQUENCE: 11

Trp Ala Ser Thr Arg Val Ser
1 5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1 5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1 5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti c-Met humanized antibody(huAbF46-H4))

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti c-Met humanized antibody (huAbF46-H4))

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti c-Met humanized antibody (huAbF46-H4))

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30
```

```
Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg


<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody (huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg


<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody (huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95
```

```
Ser Tyr Ser Arg Pro Phe Thr Phe Gly Gln Gly Thr Lys Val Glu Ile
            100                 105                 110

Lys Arg


<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5


<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5


<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5


<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5


<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5


<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)
```

<400> SEQUENCE: 27

Asp Asn Trp Leu Ser Tyr
1 5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1 5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1 5 10 15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1 5 10 15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1 5 10 15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1 5 10 15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1 5 10 15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1 5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1 5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain of chAbF46)
<220> FEATURE:
<221> NAME/KEY: misc_feature
<222> LOCATION: (1)..(6)
<223> OTHER INFORMATION: EcoRI restriction site
<220> FEATURE:

```
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38

gaattcgccg ccaccatgga atggagctgg gtttttctcg taacactttt aaatggtatc     60

cagtgtgagg tgaagctggt ggagtctgga ggaggcttgg tacagcctgg gggttctctg    120

agactctcct gtgcaacttc tgggttcacc ttcactgatt actacatgag ctgggtccgc    180

cagcctccag gaaaggcact tgagtggttg ggttttatta gaaacaaagc taatggttac    240

acaacagagt acagtgcatc tgtgaagggt cggttcacca tctccagaga taattcccaa    300

agcatcctct atcttcaaat ggacaccctg agagctgagg acagtgccac ttattactgt    360

gcaagagata actggtttgc ttactggggc caagggactc tggtcactgt ctctgcagct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga ctcgag                             1416


<210> SEQ ID NO 39
<211> LENGTH: 759
<212> TYPE: DNA
<213> ORGANISM: Artificial Sequence
```

```
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

gaattcacta gtgattaatt cgccgccacc atggattcac aggcccaggt cctcatgttg     60

ctgctgctat cggtatctgg tacctgtgga gacattttga tgacccagtc tccatcctcc    120

ctgactgtgt cagcaggaga gaaggtcact atgagctgca agtccagtca gagtctttta    180

gctagtggca accaaaataa ctacttggcc tggcaccagc agaaaccagg acgatctcct    240

aaaatgctga taatttgggc atccactagg gtatctggag tccctgatcg cttcataggc    300

agtggatctg ggacggattt cactctgacc atcaacagtg tgcaggctga agatctggct    360

gtttattact gtcagcagtc ctacagcgct ccgctcacgt tcggtgctgg gaccaagctg    420

gagctgaaac gtacggtggc tgcaccatct gtcttcatct tcccgccatc tgatgagcag    480

ttgaaatctg gaactgcctc tgttgtgtgc ctgctgaata acttctatcc cagagaggcc    540

aaagtacagt ggaaggtgga taacgccctc caatcgggta actcccagga gagtgtcaca    600

gagcaggaca gcaaggacag cacctacagc ctcagcagca ccctgacgct gagcaaagca    660

gactacgaga aacacaaagt ctacgcctgc gaagtcaccc atcagggcct gagctcgccc    720

gtcacaaaga gcttcaacag gggagagtgt tgactcgag                           759


<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45
```

```
Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 41
<211> LENGTH: 447
<212> TYPE: PRT

<213> ORGANISM: Artificial Sequence
<220> FEATURE:
<223> OTHER INFORMATION: Synthetic (amino acid sequence of H3-heavy)

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215


<210> SEQ ID NO 47
<211> LENGTH: 1350
```

<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

```
gaggtgcagc tggtggagtc tgggggaggc ttggtccagc ctggagggtc cctgagactc     60
tcctgtgcag cctctggatt caccttcact gactactaca tgagctgggt ccgccaggct    120
ccagggaagg ggctggagtg gttgggcttt attagaaaca aagctaacgg ttacaccaca    180
gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga aagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

```
gaggtgcagc tggtggagtc tgggggaggc ttggtccagc ctggagggtc cctgagactc     60
tcctgtgcag cctctggatt caccttcact gactactaca tgagctgggt ccgccaggct    120
ccagggaagg ggctggagtg gttgggcttt attagaaaca aagctaacgg ttacaccaca    180
gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
```

```
ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350
```

```
<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49
```

```
gaggttcagc tggtggagtc tggcggtggc ctggtgcagc caggggggctc actccgtttg     60

tcctgtgcag cttctggctt caccttcact gattactaca tgagctgggt gcgtcaggcc    120

ccgggtaagg gcctggaatg gttgggtttt attagaaaca aagctaatgg ttacacaaca    180

gagtacagtg catctgtgaa gggtcgtttc actataagca gagataattc caaaaacaca    240

ctgtacctgc agatgaacag cctgcgtgct gaggacactg ccgtctatta ttgtgctaga    300

gataactggt ttgcttactg gggccaaggg actctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200
```

```
gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

```
gacatcgtga tgacccagtc tccagactcc ctggctgtgt ctctgggcga gagggccacc     60

atcaactgca agtccagcca gagtctttta gctagcggca accaaaataa ctacttagct    120

tggcaccagc agaaaccagg acagcctcct aagatgctca ttatttgggc atctacccgg    180

gtatccgggg tccctgaccg attcagtggc agcgggtctg ggacagattt cactctcacc    240

atcagcagcc tgcaggctga agatgtggca gtttattact gtcagcaatc ctatagtgct    300

cctctcacgt tcggaggcgg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc     60

atctcctgca agtccagtca gagtctttta gctagtggca accaaaataa ctacttggcc    120

tggcacctgc agaagccagg gcagtctcca cagatgctga tcatttgggc atccactagg    180

gtatctggag tcccagacag gttcagtggc agtgggtcag gcactgattt cacactgaaa    240

atcagcaggg tggaggctga ggatgttgga gtttattact gccagcagtc ctacagcgct    300

ccgctcacgt tcggacaggg taccaagctg gagctcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 52
<211> LENGTH: 669
<212> TYPE: DNA

```
<213> ORGANISM: Artificial Sequence
<220> FEATURE:
<223> OTHER INFORMATION: Synthetic (nucleotide sequence of H3-light)

<400> SEQUENCE: 52

gacatcgtga tgacccagtc tccagactcc ctggctgtgt ctctgggcga gagggccacc     60

atcaactgca agtccagcca gagtctttta gctagcggca accaaaataa ctacttagct    120

tggtaccagc agaaaccagg acagcctcct aagctgctca ttatttgggc atctacccgg    180

gtatccgggg tccctgaccg attcagtggc agcgggtctg ggacagattt cactctcacc    240

atcagcagcc tgcaggctga agatgtggca gtttattact gtcagcaatc ctatagtgct    300

cctctcacgt tcggaggcgg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669


<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

gatatccaga tgacccagtc cccgagctcc ctgtccgcct ctgtgggcga tagggtcacc     60

atcacctgca agtccagtca gagtctttta gctagtggca accaaaataa ctacttggcc    120

tggcaccaac agaaaccagg aaaagctccg aaaatgctga ttatttgggc atccactagg    180

gtatctggag tcccttctcg cttctctgga tccgggtctg ggacggattt cactctgacc    240

atcagcagtc tgcagccgga agacttcgca acttattact gtcagcagtc ctacagcgct    300

ccgctcacgt tcggacaggg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669


<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Gly Ser Gly Gly Gly Gly Ser Gly
1               5                   10                  15

Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of huAbF46 antibody)

<400> SEQUENCE: 55

```
gctagcgttt tagcagaagt tcaattggtt gaatctggtg gtggtttggt tcaaccaggt     60

ggttctttga gattgtcttg tgctgcttct ggttttactt tcaccgatta ttacatgtcc    120

tgggttagac aagctccagg taaaggtttg gaatggttgg gtttcattag aaacaaggct    180

aacggttaca ctaccgaata ttctgcttct gttaagggta gattcaccat ttctagagac    240

aactctaaga acaccttgta cttgcaaatg aactccttga gagctgaaga tactgctgtt    300

tattactgcg ctagagataa ttggtttgct tattggggtc aaggtacttt ggttactgtt    360

tcttctggcc tcgggggcct cggaggagga ggtagtggcg gaggaggctc cggtggatcc    420

agcggtgtgg gttccgatat tcaaatgacc caatctccat cttctttgtc tgcttcagtt    480

ggtgatagag ttaccattac ttgtaagtcc tcccaatctt tgttggcttc tggtaatcag    540

aacaattact tggcttggca tcaacaaaaa ccaggtaaag ctccaaagat gttgattatt    600

tgggcttcta ccagagtttc tggtgttcca tctagatttt ctggttctgg ttccggtact    660

gattttactt tgaccatttc atccttgcaa ccagaagatt tcgctactta ctactgtcaa    720

caatcttact ctgctccatt gacttttggt caaggtacaa aggtcgaaat caagagagaa    780

ttcggtaagc ctatccctaa ccctctcctc ggtctcgatt ctacgggtgg tggtggatct    840

ggtggtggtg gttctggtgg tggtggttct caggaactga caactatatg cgagcaaatc    900

ccctcaccaa ctttagaatc gacgccgtac tctttgtcaa cgactactat tttggccaac    960

gggaaggcaa tgcaaggagt tttgaatat tacaaatcag taacgtttgt cagtaattgc    1020

ggttctcacc cctcaacaac tagcaaaggc agccccataa acacacagta tgttttttga   1080

gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:

<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgctagcgt tttagcagaa gttcaattgg    600

ttgaatctgg tggtggtttg gttcaaccag gtggttcttt gagattgtct tgtgctgctt    660

ctggttttac tttcaccgat tattacatgt cctgggttag acaagctcca ggtaaaggtt    720

tggaatggtt gggtttcatt agaaacaagg ctaacggtta cactaccgaa tattctgctt    780

ctgttaaggg tagattcacc atttctagag acaactctaa gaacaccttg tacttgcaaa    840

tgaactcctt gagagctgaa gatactgctg tttattactg cgctagagat aattggtttg    900

cttattgggg tcaaggtact ttggttactg tttcttctgg cctcgggggc ctcggaggag    960

gaggtagtgg cggaggaggc tccggtggat ccagcggtgt gggttccgat attcaaatga   1020

cccaatctcc atcttctttg tctgcttcag ttggtgatag agttaccatt acttgtaagt   1080

cctcccaatc tttgttggct tctggtaatc agaacaatta cttggcttgg catcaacaaa   1140

aaccaggtaa agctccaaag atgttgatta tttgggcttc taccagagtt tctggtgttc   1200

catctagatt ttctggttct ggttccggta ctgattttac tttgaccatt tcatccttgc   1260

aaccagaaga tttcgctact tactactgtc aacaatctta ctctgctcca ttgacttttg   1320

gtcaaggtac aaaggtcgaa atcaagagag aattcggtaa gcctatccct aaccctctcc   1380

tcggtctcga ttctacgggt ggtggtggat ctggtggtgg tggttctggt ggtggtggtt   1440

ctcaggaact gacaactata tgcgagcaaa tcccctcacc aactttagaa tcgacgccgt   1500

actctttgtc aacgactact attttggcca acgggaaggc aatgcaagga gtttttgaat   1560

attacaaatc agtaacgttt gtcagtaatt gcggttctca cccctcaaca actagcaaag   1620

gcagccccat aaacacacag tatgtttttt gagtttaaac ccgctgatct gataacaaca   1680

gtgtagatgt aacaaaatcg actttgttcc cactgtactt ttagctcgta caaaatacaa   1740
```

```
tatacttttc atttctccgt aaacaacatg ttttcccatg taatatcctt ttctattttt   1800

cgttccgtta ccaactttac acatacttta tatagctatt cacttctata cactaaaaaa   1860

ctaagacaat tttaattttg ctgcctgcca tatttcaatt tgttataaat tcctataatt   1920

tatcctatta gtagctaaaa aaagatgaat gtgaatcgaa tcctaagaga attgggcaag   1980

tgcacaaaca atacttaaat aaatactact cagtaataac ctatttctta gcatttttga   2040

cgaaatttgc tattttgtta gagtctttta caccatttgt ctccacacct ccgcttacat   2100

caacaccaat aacgccattt aatctaagcg catcaccaac attttctggc gtcagtccac   2160

cagctaacat aaaatgtaag ctctcggggc tctcttgcct tccaacccag tcagaaatcg   2220

agttccaatc caaaagttca cctgtcccac ctgcttctga atcaaacaag ggaataaacg   2280

aatgaggttt ctgtgaagct gcactgagta gtatgttgca gtcttttgga aatacgagtc   2340

ttttaataac tggcaaaccg aggaactctt ggtattcttg ccacgactca tctccgtgca   2400

gttggacgat atcaatgccg taatcattga ccagagccaa aacatcctcc ttaggttgat   2460

tacgaaacac gccaaccaag tatttcggag tgcctgaact atttttatat gcttttacaa   2520

gacttgaaat tttccttgca ataaccgggt caattgttct ctttctattg ggcacacata   2580

taatacccag caagtcagca tcggaatcta gagcacattc tgcggcctct gtgctctgca   2640

agccgcaaac tttcaccaat ggaccagaac tacctgtgaa attaataaca gacatactcc   2700

aagctgcctt tgtgtgctta atcacgtata ctcacgtgct caatagtcac caatgccctc   2760

cctcttggcc ctctcctttt ctttttttcga ccgaatttct tgaagacgaa agggcctcgt   2820

gatacgccta tttttatagg ttaatgtcat gataataatg gtttcttagg acggatcgct   2880

tgcctgtaac ttacacgcgc ctcgtatctt ttaatgatgg aataatttgg gaatttactc   2940

tgtgtttatt tatttttatg ttttgtattt ggattttaga aagtaaataa agaaggtaga   3000

agagttacgg aatgaagaaa aaaaaataaa caaaggttta aaaaatttca acaaaaagcg   3060

tactttacat atatatttat tagacaagaa aagcagatta aatagatata cattcgatta   3120

acgataagta aaatgtaaaa tcacaggatt ttcgtgtgtg gtcttctaca cagacaagat   3180

gaaacaattc ggcattaata cctgagagca ggaagagcaa gataaaaggt agtatttgtt   3240

ggcgatcccc ctagagtctt ttacatcttc ggaaaacaaa aactattttt tctttaattt   3300

cttttttttac tttctatttt taatttatat atttatatta aaaaatttaa attataatta   3360

tttttatagc acgtgatgaa aaggacccag gtggcacttt tcggggaaat gtgcgcggaa   3420

cccctatttg tttatttttc taaatacatt caaatatgta tccgctcatg agacaataac   3480

cctgataaat gcttcaataa tattgaaaaa ggaagagtat gagtattcaa catttccgtg   3540

tcgcccttat tccctttttt gcggcatttt gccttcctgt ttttgctcac ccagaaacgc   3600

tggtgaaagt aaaagatgct gaagatcagt tgggtgcacg agtgggttac atcgaactgg   3660

atctcaacag cggtaagatc cttgagagtt ttcgccccga agaacgtttt ccaatgatga   3720

gcacttttaa agttctgcta tgtggcgcgg tattatcccg tgttgacgcc gggcaagagc   3780

aactcggtcg ccgcatacac tattctcaga atgacttggt tgagtactca ccagtcacag   3840

aaaagcatct tacggatggc atgacagtaa gagaattatg cagtgctgcc ataaccatga   3900

gtgataacac tgcggccaac ttacttctga caacgatcgg aggaccgaag gagctaaccg   3960

cttttttgca caacatgggg gatcatgtaa ctcgccttga tcgttgggaa ccggagctga   4020

atgaagccat accaaacgac gagcgtgaca ccacgatgcc tgtagcaatg gcaacaacgt   4080
```

```
tgcgcaaact attaactggc gaactactta ctctagcttc ccggcaacaa ttaatagact   4140

ggatggaggc ggataaagtt gcaggaccac ttctgcgctc ggcccttccg gctggctggt   4200

ttattgctga taaatctgga gccggtgagc gtgggtctcg cggtatcatt gcagcactgg   4260

ggccagatgg taagccctcc cgtatcgtag ttatctacac gacgggcagt caggcaacta   4320

tggatgaacg aaatagacag atcgctgaga taggtgcctc actgattaag cattggtaac   4380

tgtcagacca agtttactca tatatacttt agattgattt aaaacttcat ttttaattta   4440

aaaggatcta ggtgaagatc ctttttgata atctcatgac caaaatccct taacgtgagt   4500

tttcgttcca ctgagcgtca gaccccgtag aaaagatcaa aggatcttct tgagatcctt   4560

tttttctgcg cgtaatctgc tgcttgcaaa caaaaaaacc accgctacca gcggtggttt   4620

gtttgccgga tcaagagcta ccaactcttt ttccgaaggt aactggcttc agcagagcgc   4680

agataccaaa tactgtcctt ctagtgtagc cgtagttagg ccaccacttc aagaactctg   4740

tagcaccgcc tacatacctc gctctgctaa tcctgttacc agtggctgct gccagtggcg   4800

ataagtcgtg tcttaccggg ttggactcaa gacgatagtt accggataag gcgcagcggt   4860

cgggctgaac ggggggttcg tgcacacagc ccagcttgga gcgaacgacc tacaccgaac   4920

tgagatacct acagcgtgag cattgagaaa gcgccacgct tcccgaaggg agaaaggcgg   4980

acaggtatcc ggtaagcggc agggtcggaa caggagagcg cacgagggag cttccagggg   5040

ggaacgcctg gtatctttat agtcctgtcg ggtttcgcca cctctgactt gagcgtcgat   5100

ttttgtgatg ctcgtcaggg gggcgagcc tatggaaaaa cgccagcaac gcggcctttt   5160

tacggttcct ggccttttgc tggccttttg ctcacatgtt ctttcctgcg ttatcccctg   5220

attctgtgga taaccgtatt accgcctttg agtgagctga taccgctcgc cgcagccgaa   5280

cgaccgagcg cagcgagtca gtgagcgagg aagcggaaga gcgcccaata cgcaaaccgc   5340

ctctccccgc gcgttggccg attcattaat gcagctggca cgacaggttt cccgactgga   5400

aagcgggcag tgagcgcaac gcaattaatg tgagttacct cactcattag gcaccccagg   5460

ctttacactt tatgcttccg gctcctatgt tgtgtggaat tgtgagcgga taacaatttc   5520

acacaggaaa cagctatgac catgattacg ccaagctcgg aattaaccct cactaaaggg   5580

aacaaaagct ggctagt                                                  5597
```

```
<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10


<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58

gaattcacta gtgattaatt cgccgccacc atggattcac aggcccaggt cctcatgttg     60

ctgctgctat cggtatctgg tacctgtgga gatatccaga tgacccagtc cccgagctcc    120
```

```
ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtcagcagtc ctacagccgc ccgtacacgt tcggacaggg taccaaggtg    420

gagatcaaac gtacg                                                     435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-2 clone)

<400> SEQUENCE: 59

```
gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtgggcagtc ctacagccgt ccgctcacgt tcggacaggg taccaaggtg    420

gagatcaaac gtacg                                                     435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-3 clone)

<400> SEQUENCE: 60

```
gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtgcacagtc ctacagccat ccgttctctt tcggacaggg taccaaggtg    420

gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

```
gaattcacta gtgattaatt cgccgccacc atggattcac aggcccaggt cctcatgttg     60
```

```
ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtcagcagtc ctacagccgc ccgtttacgt tcggacaggg taccaaggtg    420

gagatcaaac gtacg                                                     435
```

```
<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region of human
      IgG1)

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
```

```
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, U6-HC7 hinge and constant region of human IgG1)

<400> SEQUENCE: 63

```
gaattcgccg ccaccatgga atggagctgg gtttttctcg taacactttt aaatggtatc      60

cagtgtgagg ttcagctggt ggagtctggc ggtggcctgg tgcagccagg gggctcactc     120

cgtttgtcct gtgcagcttc tggcttcacc ttcactgatt actacatgag ctgggtgcgt     180

caggccccgg gtaagggcct ggaatggttg ggttttatta gaaacaaagc taatggttac     240

acaacagagt acagtgcatc tgtgaagggt cgtttcacta taagcagaga taattccaaa     300

aacacactgt acctgcagat gaacagcctg cgtgctgagg acactgccgt ctattattgt     360

gctagagata actggtttgc ttactggggc caagggactc tggtcaccgt ctcctcggct     420

agcaccaagg gcccatcggt cttccccctg gcaccctcct ccaagagcac ctctgggggc     480

acagcggccc tgggctgcct ggtcaaggac tacttccccg aaccggtgac ggtgtcgtgg     540

aactcaggcg ccctgaccag cggcgtgcac accttcccgg ctgtcctaca gtcctcagga     600

ctctactccc tcagcagcgt ggtgaccgtg ccctccagca gcttgggcac ccagacctac     660

atctgcaacg tgaatcacaa gcccagcaac accaaggtgg acaagaaagt tgagcccaaa     720

agctgcgatt gccactgtcc tccatgtcca gcacctgaac tcctgggggg accgtcagtc     780

ttcctcttcc ccccaaaacc caaggacacc ctcatgatct cccggacccc tgaggtcaca     840

tgcgtggtgg tggacgtgag ccacgaagac cctgaggtca agttcaactg gtacgtggac     900

ggcgtggagg tgcataatgc caagacaaag ccgcgggagg agcagtacaa cagcacgtac     960
```

```
cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atgactcgag                                     1410


<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG1)

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270
```

```
Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2 hinge and
      constant region of human IgG1)

<400> SEQUENCE: 65

gaattcgccg ccaccatgga atggagctgg gtttttctcg taacactttt aaatggtatc     60

cagtgtgagg ttcagctggt ggagtctggc ggtggcctgg tgcagccagg gggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagaggaag    720

tgctgtgtgg agtgcccccc ctgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960
```

```
gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggaggagat gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaatg actcgag                                      1407
```

```
<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG2)

<400> SEQUENCE: 66

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270
```

```
Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, human IgG2 hinge and constant region of human IgG2)

<400> SEQUENCE: 67

```
gaattcgccg ccaccatgga atggagctgg gtttttctcg taacactttt aaatggtatc     60

cagtgtgagg ttcagctggt ggagtctggc ggtggcctgg tgcagccagg gggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900
```

```
gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140

gtcagcctga cctgcctggt caaaggcttc taccccagcg acatcgccgt ggagtgggag   1200

agcaatgggc agccggagaa caactacaag accacgcctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatgact cgag                                          1404


<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 69
<211> LENGTH: 758
<212> TYPE: DNA
<213> ORGANISM: Artificial Sequence
```

```
<220> FEATURE:
<223> OTHER INFORMATION: Synthetic (polynucleotide encoding polypeptide
      consisting of light chain of huAbF46-H4-A1(H36Y) and human kappa
      constant region)

<400> SEQUENCE: 69

aattcactag tgattaattc gccgccacca tggattcaca ggcccaggtc ctcatgttgc      60

tgctgctatc ggtatctggt acctgtggag atatccagat gacccagtcc ccgagctccc     120

tgtccgcctc tgtgggcgat agggtcacca tcacctgcaa gtccagtcag agtcttttag     180

ctagtggcaa ccaaaataac tacttggcct ggtaccaaca gaaaccagga aaagctccga     240

aaatgctgat tatttgggca tccactaggg tatctggagt cccttctcgc ttctctggat     300

ccgggtctgg gacggatttc actctgacca tcagcagtct gcagccggaa gacttcgcaa     360

cttattactg tcagcagtcc tacagccgcc cgtacacgtt cggacagggt accaaggtgg     420

agatcaaacg tacggtggct gcaccatctg tcttcatctt cccgccatct gatgagcagt     480

tgaaatctgg aactgcctct gttgtgtgcc tgctgaataa cttctatccc agagaggcca     540

aagtacagtg gaaggtggat aacgccctcc aatcgggtaa ctcccaggag agtgtcacag     600

agcaggacag caaggacagc acctacagcc tcagcagcac cctgacgctg agcaaagcag     660

actacgagaa acacaaagtc tacgcctgcg aagtcaccca tcagggcctg agctcgcccg     720

tcacaaagag cttcaacagg ggagagtgtt gactcgag                             758


<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190
```

```
Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu


<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10


<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5


<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of anti-
      c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95
```

```
Tyr Cys Ala Arg Asp Asn Trp Phe Ala Tyr Trp Gly Gln Gly Thr Leu
            100                 105                 110

Val Thr Val Ser Ser
        115


<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of anti-
      c-Met antibody (AbF46 or huAbF46-H1))

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg


<210> SEQ ID NO 76
<211> LENGTH: 1416
<212> TYPE: DNA
<213> ORGANISM: Artificial Sequence
<220> FEATURE:
<223> OTHER INFORMATION: Synthethic (nucleotide sequence of heavy chain
      of nti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
```

```
gaattcgccg ccaccatgga atggagctgg gtttttctcg taacactttt aaatggtatc     60

cagtgtgagg tgaagctggt ggagtctgga ggaggcttgg tacagcctgg gggttctctg    120

agactctcct gtgcaacttc tgggttcacc ttcactgatt actacatgag ctgggtccgc    180

cagcctccag gaaaggcact tgagtggttg ggttttatta gaaacaaagc taatggttac    240

acaacagagt acagtgcatc tgtgaagggt cggttcacca tctccagaga taattcccaa    300

agcatcctct atcttcaaat ggacaccctg agagctgagg acagtgccac ttattactgt    360

gcaagagata actggtttgc ttactggggc caagggactc tggtcactgt ctctgcagct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga ctcgag                             1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference

```
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

gaattcacta gtgattaatt cgccgccacc atggattcac aggcccaggt cctcatgttg     60

ctgctgctat cggtatctgg tacctgtgga gacattttga tgacccagtc tccatcctcc    120

ctgactgtgt cagcaggaga gaaggtcact atgagctgca agtccagtca gagtctttta    180

gctagtggca accaaaataa ctacttggcc tggcaccagc agaaaccagg acgatctcct    240

aaaatgctga taatttgggc atccactagg gtatctggag tccctgatcg cttcataggc    300

agtggatctg ggacggattt cactctgacc atcaacagtg tgcaggctga agatctggct    360

gtttattact gtcagcagtc ctacagcgct ccgctcacgt tcggtgctgg gaccaagctg    420

gagctgaaac gtacggtggc tgcaccatct gtcttcatct tcccgccatc tgatgagcag    480

ttgaaatctg gaactgcctc tgttgtgtgc ctgctgaata acttctatcc cagagaggcc    540

aaagtacagt ggaaggtgga taacgccctc caatcgggta actcccagga gagtgtcaca    600

gagcaggaca gcaaggacag cacctacagc ctcagcagca ccctgacgct gagcaaagca    660

gactacgaga aacacaaagt ctacgcctgc gaagtcaccc atcagggcct gagctcgccc    720

gtcacaaaga gcttcaacag gggagagtgt tgactcgag                           759


<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78

atgaaggccc ccgctgtgct tgcacctggc atcctcgtgc tcctgtttac cttggtgcag     60

aggagcaatg gggagtgtaa agaggcacta gcaaagtccg agatgaatgt gaatatgaag    120

tatcagcttc ccaacttcac cgcggaaaca cccatccaga atgtcattct acatgagcat    180

cacattttcc ttggtgccac taactacatt tatgttttaa atgaggaaga ccttcagaag    240

gttgctgagt acaagactgg gcctgtgctg gaacacccag attgtttccc atgtcaggac    300

tgcagcagca aagccaattt atcaggaggt gtttggaaag ataacatcaa catggctcta    360

gttgtcgaca cctactatga tgatcaactc attagctgtg gcagcgtcaa cagagggacc    420

tgccagcgac atgtctttcc ccacaatcat actgctgaca tacagtcgga ggttcactgc    480

atattctccc cacagataga agagcccagc cagtgtcctg actgtgtggt gagcgccctg    540

ggagccaaag tcctttcatc tgtaaaggac cggttcatca acttctttgt aggcaatacc    600

ataaattctt cttatttccc agatcatcca ttgcattcga tatcagtgag aaggctaaag    660

gaaacgaaag atggttttat gtttttgacg gaccagtcct acattgatgt tttacctgag    720

ttcagagatt cttaccccat taagtatgtc catgcctttg aaagcaacaa ttttatttac    780

ttcttgacgg tccaaaggga aactctagat gctcagactt ttcacacaag aataatcagg    840

ttctgttcca taaactctgg attgcattcc tacatggaaa tgcctctgga gtgtattctc    900

acagaaaaga gaaaaaagag atccacaaag aaggaagtgt ttaatatact tcaggctgcg    960

tatgtcagca agcctggggc ccagcttgct agacaaatag gagccagcct gaatgatgac   1020
```

```
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcatttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata ataaatttga tttaaagaaa   1800
actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg tttttcctgt ggctgaaaaa gagaaagcaa   2880
attaaagatc tgggcagtga attagttcgc tacgatgcaa gagtacacac tcctcatttg   2940
gataggcttg taagtgcccg aagtgtaagc ccaactacag aaatggtttc aaatgaatct   3000
gtagactacc gagctacttt tccagaagat cagtttccta attcatctca gaacggttca   3060
tgccgacaag tgcagtatcc tctgacagac atgtccccca tcctaactag tggggactct   3120
gatatatcca gtccattact gcaaaatact gtccacattg acctcagtgc tctaaatcca   3180
gagctggtcc aggcagtgca gcatgtagtg attgggccca gtagcctgat tgtgcatttc   3240
aatgaagtca taggaagagg gcattttggt tgtgtatatc atgggacttt gttggacaat   3300
gatggcaaga aaattcactg tgctgtgaaa tccttgaaca gaatcactga cataggagaa   3360
```

-continued

```
gtttcccaat ttctgaccga gggaatcatc atgaaagatt ttagtcatcc caatgtcctc   3420

tcgctcctgg gaatctgcct gcgaagtgaa gggtctccgc tggtggtcct accatacatg   3480

aaacatggag atcttcgaaa tttcattcga aatgagactc ataatccaac tgtaaaagat   3540

cttattggct ttggtcttca agtagccaaa ggcatgaaat atcttgcaag caaaaagttt   3600

gtccacagag acttggctgc aagaaactgt atgctggatg aaaaattcac agtcaaggtt   3660

gctgattttg gtcttgccag agacatgtat gataaagaat actatagtgt acacaacaaa   3720

acaggtgcaa agctgccagt gaagtggatg gctttggaaa gtctgcaaac tcaaaagttt   3780

accaccaagt cagatgtgtg gtcctttggc gtgctcctct gggagctgat gacaagagga   3840

gccccacctt atcctgacgt aaacaccttt gatataactg tttacttgtt gcaagggaga   3900

agactcctac aacccgaata ctgcccagac cccttatatg aagtaatgct aaaatgctgg   3960

caccctaaag ccgaaatgcg cccatccttt tctgaactgg tgtcccggat atcagcgatc   4020

ttctctactt tcattgggga gcactatgtc catgtgaacg ctacttatgt gaacgtaaaa   4080

tgtgtcgctc cgtatccttc tctgttgtca tcagaagata acgctgatga tgaggtggac   4140

acacgaccag cctccttctg ggagacatca                                    4170
```

```
<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220
```

```
Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440


<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140
```

```
Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450
```

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

```
Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45
```

```
Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

```
<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82

ctacatgagc atcacatttt ccttggtgcc actaactaca tttatgtttt aaatgaggaa     60

gaccttcaga aggttgctga gtacaagact gggcctgtgc tggaacaccc agattgtttc    120

ccatgtcagg actgcagcag caaagccaat ttatcaggag gtgtttggaa agataacatc    180

aacatggctc tagttgtcga cacctactat gatgatcaac tcattagctg tggcagcgtc    240

aacagaggga cctgccagcg acatgtcttt ccccacaatc atactgctga catacagtcg    300

gaggttcact gcatattctc cccacagata gaagagccca gccagtgtcc tgactgtgtg    360

gtgagcgccc tgggagccaa agtcctttca tctgtaaagg accggttcat caacttcttt    420

gtaggcaata ccataaattc ttcttatttc ccagatcatc cattgcattc gatatcagtg    480
```

```
agaaggctaa aggaaacgaa agatggtttt atgtttttga cggaccagtc ctacattgat    540

gttttacctg agttcagaga ttcttacccc attaagtatg tccatgcctt tgaaagcaac    600

aattttattt acttcttgac ggtccaaagg gaaactctag atgctcagac ttttcacaca    660

agaataatca ggttctgttc cataaactct ggattgcatt cctacatgga aatgcctctg    720

gagtgtattc tcacagaaaa gagaaaaaag agatccacaa agaaggaagt gtttaatata    780

cttcaggctg cgtatgtcag caagcctggg gcccagcttg ctagacaaat aggagccagc    840

ctgaatgatg acattctttt cggggtgttc gcacaaagca agccagattc tgccgaacca    900

atggatcgat ctgccatgtg tgcattccct atcaaatatg tcaacgactt cttcaacaag    960

atcgtcaaca aaaacaatgt gagatgtctc cagcattttt acggacccaa tcatgagcac   1020

tgctttaata ggacacttct gagaaattca tcaggctgtg aagcgcgccg tgatgaatat   1080

cgaacagagt ttaccacagc tttgcagcgc gttgacttat tcatgggtca attcagcgaa   1140

gtcctcttaa catctatatc caccttcatt aaaggagacc tcaccatagc taatcttggg   1200

acatcagagg gtcgcttcat gcaggttgtg gtttctcgat caggaccatc aacccctcat   1260

gtgaattttc tcctggactc ccatccagtg tctccagaag tgattgtgga gcatacatta   1320

aaccaaaatg gc                                                       1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT domain of c-Met)

<400> SEQUENCE: 83

```
tacacactgg ttatcactgg gaagaagatc acgaagatcc cattgaatgg cttgggctgc     60

agacatttcc agtcctgcag tcaatgcctc tctgccccac cctttgttca gtgtggctgg    120

tgccacgaca aatgtgtgcg atcggaggaa tgcctgagcg ggacatggac tcaacagatc    180

tgtctgcctg caatctacaa ggttttccca aatagtgcac cccttgaagg agggacaagg    240

ctgaccatat gtggctggga ctttggattt cggaggaata ataaatttga tttaaagaaa    300

actagagttc tccttggaaa tgagagctgc accttgactt taagtgagag cacgatgaat    360

acattgaaat gcacagttgg tcctgccatg aataagcatt tcaatatgtc cataattatt    420

tcaaatggcc acgggacaac acaatacagt acattctcct atgtggatcc tgtaataaca    480

agtatttcgc cgaaatacgg tcctatggct ggtggcactt tacttacttt aactggaaat    540

tacctaaaca gtgggaattc tagacacatt tcaattggtg gaaaaacatg tactttaaaa    600

agtgtgtcaa acagtattct tgaatgttat accccagccc aaaccatttc aactgagttt    660

gctgttaaat tgaaaattga cttagccaac cgagagacaa gcatcttcag ttaccgtgaa    720

gatcccattg tctatgaaat tcatccaacc aaatctttta ttagtggtgg gagcacaata    780

acaggtgttg ggaaaaacct gaattcagtt agtgtcccga gaatggtcat aaatgtgcat    840

gaagcaggaa ggaactttac agtggcatgt caacatcgct ctaattcaga gataatctgt    900

tgtaccactc cttccctgca acagctgaat ctgcaactcc ccctgaaaac caaagccttt    960

ttcatgttag atgggatcct ttccaaatac tttgatctca tttatgtaca taatcctgtg   1020

tttaagcctt ttgaaaagcc agtgatgatc tcaatgggca atgaaaatgt actggaaatt   1080

aagggaaatg atattgaccc tgaagcagtt aaaggtgaag tgttaaaagt tggaaataag   1140
```

```
agctgtgaga atatacactt acattctgaa gccgttttat gcacggtccc caatgacctg   1200

ctgaaattga acagcgagct aaatatagag tggaagcaag caatttcttc aaccgtcctt   1260

ggaaaagtaa tagttcaacc agatcagaat ttcacagga                          1299


<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84

gtgcatttca atgaagtcat aggaagaggg cattttggtt gtgtatatca tgggactttg     60

ttggacaatg atggcaagaa aattcactgt gctgtgaaat ccttgaacag aatcactgac    120

ataggagaag tttcccaatt tctgaccgag ggaatcatca tgaaagattt tagtcatccc    180

aatgtcctct cgctcctggg aatctgcctg cgaagtgaag ggtctccgct ggtggtccta    240

ccatacatga aacatggaga tcttcgaaat ttcattcgaa atgagactca taatccaact    300

gtaaaagatc ttattggctt tggtcttcaa gtagccaaag gcatgaaata tcttgcaagc    360

aaaaagtttg tccacagaga cttggctgca agaaactgta tgctggatga aaaattcaca    420

gtcaaggttg ctgattttgg tcttgccaga gacatgtatg ataaagaata ctatagtgta    480

cacaacaaaa caggtgcaaa gctgccagtg aagtggatgg ctttggaaag tctgcaaact    540

caaaagttta ccaccaagtc agatgtgtgg tcctttggcg tgctcctctg ggagctgatg    600

acaagaggag ccccacctta tcctgacgta aacacctttg atataactgt ttacttgttg    660

caagggagaa gactcctaca acccgaatac tgcccagacc ccttatatga agtaatgcta    720

aaatgctggc accctaaagc cgaaatgcgc ccatcctttt ctgaactggt gtcccggata    780

tcagcgatct tctctacttt cattggggag cactatgtcc atgtgaacgc tacttatgtg    840

aacgtaaaat gtgtcgctcc gtatccttct ctgttgtcat cagaagataa cgctgatgat    900

gaggtggaca cacgaccagc ctccttctgg gagacatca                           939


<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met
      antibody)

<400> SEQUENCE: 85

Asp Asn Trp Phe Ala Tyr Trp Gly Gln Gly Thr Leu Val
1               5                   10


<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 86

Leu Thr Phe Gly Ala Gly Thr Lys Leu Glu
1               5                   10


<210> SEQ ID NO 87
```

<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

Glu Val Lys Leu Val Glu Ser Gly Gly Gly Leu Val Gln Pro Gly Gly
1 5 10 15

Ser Leu Arg Leu Ser Cys Ala Thr Ser Gly Phe Thr Phe Thr Asp Tyr
20 25 30

Tyr Met Ser Trp Val Arg Gln Pro Pro Gly Lys Ala Leu Glu Trp Leu
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asn Ser Gln Ser Ile
65 70 75 80

Leu Tyr Leu Gln Met Asp Thr Leu Arg Ala Glu Asp Ser Ala Thr Tyr
85 90 95

Tyr Cys Ala Arg Asp Asn Trp Phe Ala Tyr Trp Gly Gln Gly Thr Leu
100 105 110

Val Thr Val Ser Ala
115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of anti-c-Met antibody)

<400> SEQUENCE: 88

Asp Ile Leu Met Thr Gln Ser Pro Ser Ser Leu Thr Val Ser Ala Gly
1 5 10 15

Glu Lys Val Thr Met Ser Cys Lys Ser Ser Gln Ser Leu Leu Ala Ser
20 25 30

Gly Asn Gln Asn Asn Tyr Leu Ala Trp His Gln Gln Lys Pro Gly Arg
35 40 45

Ser Pro Lys Met Leu Ile Ile Trp Ala Ser Thr Arg Val Ser Gly Val
50 55 60

Pro Asp Arg Phe Ile Gly Ser Gly Ser Gly Thr Asp Phe Thr Leu Thr
65 70 75 80

Ile Asn Ser Val Gln Ala Glu Asp Leu Ala Val Tyr Tyr Cys Gln Gln
85 90 95

Ser Tyr Ser Ala Pro Leu Thr Phe Gly Ala Gly Thr Lys Leu Glu Leu
100 105 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 89

Gln Gln Ser Tyr Ser Ala Pro Leu Thr Phe Gly Ala Gly Thr Lys Leu

```
1               5                   10                  15

Glu


<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of AT-
      VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 92
<211> LENGTH: 117
<212> TYPE: PRT
<213> ORGANISM: Artificial Sequence
```

<220> FEATURE:
<223> OTHER INFORMATION: Synthetic (heavy chain variable region of AT-VH3)

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of AT-VH4)

<400> SEQUENCE: 93

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of AT-VH5)

<400> SEQUENCE: 94

```
Glu Val Gln Leu Val Glu Ser Gly Gly Gly Leu Val Gln Pro Gly Gly
1               5                   10                  15
```

```
Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg


<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of AT-
      Vk1)

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
```

```
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys


<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of AT-
      Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys


<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of AT-
      Vk3)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

```
<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of AT-
      Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys


<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10


<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10


<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10


<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))
```

<400> SEQUENCE: 103

```
Glu Pro Arg Asp Cys Gly Cys Lys Pro Cys Pro Pro Cys Pro
1               5                   10
```

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

```
Glu Lys Cys Asp Lys Thr His Thr Cys Pro Pro Cys Pro
1               5                   10
```

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

```
Glu Pro Lys Ser Cys Asp Lys Thr His Thr Cys Pro Pro Cys Pro
1               5                   10                  15
```

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

```
Lys Ser Ser Gln Ser Leu Leu Ala Trp Gly Asn Gln Asn Asn Tyr Leu
1               5                   10                  15

Ala
```

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain variable region of antibody L3-11Y)

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110
```

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain of antibody L3-11Y)

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 109
<211> LENGTH: 1338
<212> TYPE: PRT
<213> ORGANISM: Artificial Sequence
<220> FEATURE:
<223> OTHER INFORMATION: Synthetic (human VEGFR-1)

<400> SEQUENCE: 109

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80
```

```
Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495
```

```
Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
```

```
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                 1005

Gly Met  Glu Phe Leu Ser Ser  Arg Lys Cys Ile His  Arg Asp Leu
    1010                 1015                 1020

Ala Ala  Arg Asn Ile Leu Leu  Ser Glu Asn Asn Val  Val Lys Ile
    1025                 1030                 1035

Cys Asp  Phe Gly Leu Ala Arg  Asp Ile Tyr Lys Asn  Pro Asp Tyr
    1040                 1045                 1050

Val Arg  Lys Gly Asp Thr Arg  Leu Pro Leu Lys Trp  Met Ala Pro
    1055                 1060                 1065

Glu Ser  Ile Phe Asp Lys Ile  Tyr Ser Thr Lys Ser  Asp Val Trp
    1070                 1075                 1080

Ser Tyr  Gly Val Leu Leu Trp  Glu Ile Phe Ser Leu  Gly Gly Ser
    1085                 1090                 1095

Pro Tyr  Pro Gly Val Gln Met  Asp Glu Asp Phe Cys  Ser Arg Leu
    1100                 1105                 1110

Arg Glu  Gly Met Arg Met Arg  Ala Pro Glu Tyr Ser  Thr Pro Glu
    1115                 1120                 1125

Ile Tyr  Gln Ile Met Leu Asp  Cys Trp His Arg Asp  Pro Lys Glu
    1130                 1135                 1140

Arg Pro  Arg Phe Ala Glu Leu  Val Glu Lys Leu Gly  Asp Leu Leu
    1145                 1150                 1155

Gln Ala  Asn Val Gln Gln Asp  Gly Lys Asp Tyr Ile  Pro Ile Asn
    1160                 1165                 1170

Ala Ile  Leu Thr Gly Asn Ser  Gly Phe Thr Tyr Ser  Thr Pro Ala
    1175                 1180                 1185

Phe Ser  Glu Asp Phe Phe Lys  Glu Ser Ile Ser Ala  Pro Lys Phe
    1190                 1195                 1200

Asn Ser  Gly Ser Ser Asp Asp  Val Arg Tyr Val Asn  Ala Phe Lys
    1205                 1210                 1215

Phe Met  Ser Leu Glu Arg Ile  Lys Thr Phe Glu Glu  Leu Leu Pro
    1220                 1225                 1230

Asn Ala  Thr Ser Met Phe Asp  Asp Tyr Gln Gly Asp  Ser Ser Thr
    1235                 1240                 1245

Leu Leu  Ala Ser Pro Met Leu  Lys Arg Phe Thr Trp  Thr Asp Ser
    1250                 1255                 1260

Lys Pro  Lys Ala Ser Leu Lys  Ile Asp Leu Arg Val  Thr Ser Lys
    1265                 1270                 1275

Ser Lys  Glu Ser Gly Leu Ser  Asp Val Ser Arg Pro  Ser Phe Cys
    1280                 1285                 1290

His Ser  Ser Cys Gly His Val  Ser Glu Gly Lys Arg  Arg Phe Thr
    1295                 1300                 1305

Tyr Asp  His Ala Glu Leu Glu  Arg Lys Ile Ala Cys  Cys Ser Pro
    1310                 1315                 1320
```

```
Pro Pro  Asp Tyr Asn Ser Val  Val Leu Tyr Ser Thr  Pro Pro Ile
    1325                 1330                 1335


<210> SEQ ID NO 110
<211> LENGTH: 101
<212> TYPE: PRT
<213> ORGANISM: Artificial Sequence
<220> FEATURE:
<223> OTHER INFORMATION: Synthetic (amino acid sequence of Ig2
      domain(VIG2) of human VEGF receptor 1)

<400> SEQUENCE: 110

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile
            100


<210> SEQ ID NO 111
<211> LENGTH: 303
<212> TYPE: DNA
<213> ORGANISM: Artificial Sequence
<220> FEATURE:
<223> OTHER INFORMATION: Synthetic (coding sequence of VIG2)

<400> SEQUENCE: 111

agtgatacag gtagaccttt cgtagagatg tacagtgaaa tccccgaaat tatacacatg      60

actgaaggaa gggagctcgt cattccctgc cgggttacgt cacctaacat cactgttact     120

ttaaaaaagt ttccacttga cactttgatc cctgatggaa aacgcataat ctgggacagt     180

agaaagggct tcatcatatc aaatgcaacg tacaaagaaa tagggcttct gacctgtgaa     240

gcaacagtca atgggcattt gtataagaca aactatctca cacatcgaca aaccaataca     300

atc                                                                   303


<210> SEQ ID NO 112
<211> LENGTH: 442
<212> TYPE: PRT
<213> ORGANISM: Artificial Sequence
<220> FEATURE:
<223> OTHER INFORMATION: Synthetic (heavy chain of anti-c-Met antibody
      1)

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Arg Gly Thr Thr Tyr Asn Gln Lys Phe
```

```
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

<210> SEQ ID NO 113
<211> LENGTH: 215
<212> TYPE: PRT
<213> ORGANISM: Artificial Sequence
<220> FEATURE:
<223> OTHER INFORMATION: Synthetic (light chain of anti-c-Met antibody 1)

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Asp Cys
    210                 215
```

<210> SEQ ID NO 114
<211> LENGTH: 446
<212> TYPE: PRT
<213> ORGANISM: Artificial Sequence
<220> FEATURE:
<223> OTHER INFORMATION: Synthetic (heavy chain of anti-c-Met antibody 2)

<400> SEQUENCE: 114

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Asp Trp Met
        35                  40                  45

Gly Gly Ile Lys Pro Asn Asn Gly Leu Ala Asn Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110
```

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Cys His
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 115
<211> LENGTH: 218
<212> TYPE: PRT
<213> ORGANISM: Artificial Sequence
<220> FEATURE:
<223> OTHER INFORMATION: Synthetic (light chain of anti-c-Met antibody
      2)

<400> SEQUENCE: 115

Asp Ile Val Leu Thr Gln Ser Pro Asp Ser Leu Ala Val Ser Leu Gly
1               5                   10                  15

Glu Arg Ala Thr Ile Asn Cys Arg Ser Ser Glu Ser Val Asp Ser Tyr
```

```
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 116
<211> LENGTH: 5
<212> TYPE: PRT
<213> ORGANISM: Artificial Sequence
<220> FEATURE:
<223> OTHER INFORMATION: Synthetic (G4S linker)

<400> SEQUENCE: 116

Gly Gly Gly Gly Ser
1               5


<210> SEQ ID NO 117
<211> LENGTH: 10
<212> TYPE: PRT
<213> ORGANISM: Artificial Sequence
<220> FEATURE:
<223> OTHER INFORMATION: Synthetic ((G4S)2 linker)

<400> SEQUENCE: 117

Gly Gly Gly Gly Ser Gly Gly Gly Gly Ser
1               5                   10


<210> SEQ ID NO 118
<211> LENGTH: 20
<212> TYPE: PRT
<213> ORGANISM: Artificial Sequence
<220> FEATURE:
<223> OTHER INFORMATION: Synthetic ((G4S)4 linker)

<400> SEQUENCE: 118

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 119
<211> LENGTH: 114
<212> TYPE: PRT
<213> ORGANISM: Artificial Sequence
<220> FEATURE:
<223> OTHER INFORMATION: Synthetic (light chain variable region of anti
      c-Met antibody)

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```